United States Patent
Wookey et al.

(10) Patent No.: US 10,379,127 B2
(45) Date of Patent: Aug. 13, 2019

(54) MARKER OF CELL DEATH

(71) Applicant: WELCOME RECEPTOR ANTIBODIES PTY LTD, North Melbourne, Victoria (AU)

(72) Inventors: Peter John Wookey, North Melbourne (AU); Sebastian George Barton Furness, Coburg North (AU)

(73) Assignee: WELCOME RECEPTOR ANTIBODIES PTY LTD, North Melbourne, Victoria (AU)

( * ) Notice: Subject to any disclaimer, the term of this patent is extended or adjusted under 35 U.S.C. 154(b) by 132 days.

(21) Appl. No.: 15/037,360

(22) PCT Filed: Nov. 27, 2014

(86) PCT No.: PCT/AU2014/001081
§ 371 (c)(1),
(2) Date: May 18, 2016

(87) PCT Pub. No.: WO2015/077826
PCT Pub. Date: Jun. 4, 2015

(65) Prior Publication Data
US 2016/0274132 A1    Sep. 22, 2016

(30) Foreign Application Priority Data
Nov. 27, 2013  (AU) ................ 2013904574

(51) Int. Cl.
| | |
|---|---|
| *A61K 49/00* | (2006.01) |
| *G01N 33/74* | (2006.01) |
| *C07K 16/28* | (2006.01) |
| *G01N 33/58* | (2006.01) |

(52) U.S. Cl.
CPC ............ *G01N 33/74* (2013.01); *A61K 49/00* (2013.01); *C07K 16/2869* (2013.01); *G01N 33/582* (2013.01); *C07K 2317/34* (2013.01); *C07K 2317/565* (2013.01); *C07K 2317/76* (2013.01); *G01N 2333/585* (2013.01); *G01N 2333/72* (2013.01); *G01N 2500/10* (2013.01); *G01N 2510/00* (2013.01); *G01N 2800/52* (2013.01)

(58) Field of Classification Search
CPC ............ A61K 2121/00; A61K 2123/00; A61K 49/00; G01N 33/74; G01N 33/582; G01N 2333/585; G01N 2800/52; G01N 2510/00; G01N 2500/10; G01N 2333/72; C07K 16/2869; C07K 2317/565; C07K 2317/76; C07K 2317/34

USPC .......... 424/1.11, 1.49, 1.65, 1.69, 1.81, 1.85, 424/1.89, 9.1, 9.2, 9.3, 9.4, 9.5, 9.6; 514/1, 1.1

See application file for complete search history.

(56) References Cited

U.S. PATENT DOCUMENTS

| | | | |
|---|---|---|---|
| 8,530,628 B2 * | 9/2013 | Wookey ............ | C07K 16/2869 435/7.1 |
| 2010/0111932 A1 | 5/2010 | Skerry et al. | |
| 2011/0150870 A1 | 6/2011 | Rader et al. | |

FOREIGN PATENT DOCUMENTS

| | | |
|---|---|---|
| WO | 2008009545 | 6/2008 |
| WO | 2009039584 | 4/2009 |
| WO | 2011139985 | 11/2011 |

OTHER PUBLICATIONS

Wookey et al, "Calcitonin receptor immunoreactivity associated with specific cell types in diseased radial and internal mammary arteries" Histopathology, vol. 52, No. 5, Apr. 1, 2008, pp. 605-612.
Wookey et al, "The expression of calcitonin receptor detected in malignant cells of the brain tumour glioblastoma multiforme and functional properties in the cell line A172", Histopathology., vol. 60, No. 6, Apr. 15, 2012, pp. 895-910.
European Patent Application No. 14865890.9, "Extended European Search Report" dated Feb. 1, 2017, 14 pages.
Kuo et al., "Calcitonin inhibits SDCP-induced osteoclast apoptosis and increases its efficacy in a rat model of osteoporosis", PloS one 7.7 (2012): e40272.
International Patent Application No. PCT/AU2014/001081, "Written Opinion" dated Dec. 22, 2014.
International Patent Application No. PCT/AU2014/001081, "International Search Report" dated Dec. 22, 2014.

* cited by examiner

*Primary Examiner* — D. L. Jones
(74) *Attorney, Agent, or Firm* — Kilpatrick Townsend & Stockton, LLP

(57) ABSTRACT

The present invention relates to methods for detecting cell death in a cell or a sample comprising cells, or in cultured cells in vitro by detecting the level of calcitonin receptor. The present invention also relates to methods of imaging cell death in a subject, compositions useful for detecting cell death in a cell or in a subject, methods of screening for modulators of cell death, and methods of staging and monitoring the progress of disease by detecting cell death.

11 Claims, 10 Drawing Sheets

Figure 1:
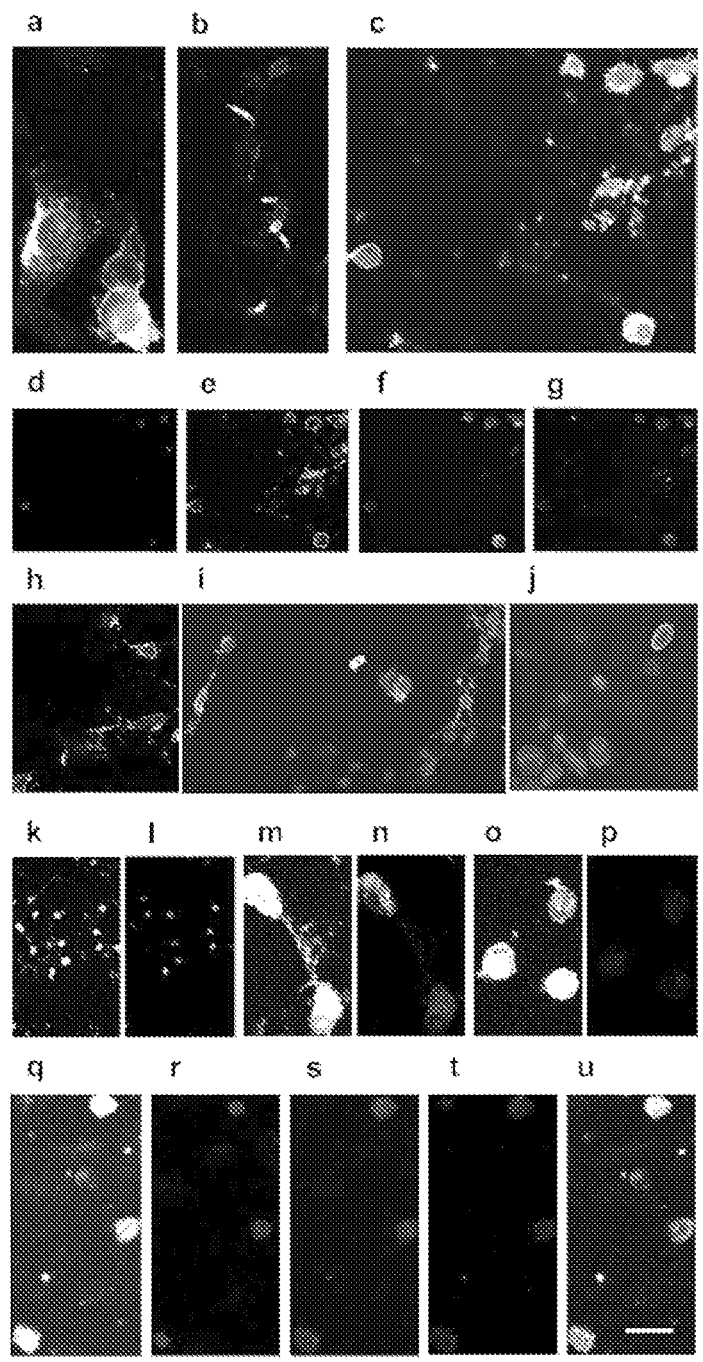

Specification includes a Sequence Listing.

MARKER OF CELL DEATH

PRIOR RELATED APPLICATIONS

This application is a National Phase application of International Application No. PCT/AU2014/001081, filed Nov. 27, 2014, which claims priority to Australian Application No. 2013904574, filed Nov. 27, 2013, each of which is incorporated herein by reference in its entirety.

FIELD OF THE INVENTION

The present invention relates to methods for detecting cell death in a cell or a sample comprising cells, or in cultured cells in vitro. The present invention also relates to methods of imaging cell death in a subject, compositions useful for detecting cell death in a cell or in a subject, methods of screening for modulators of cell death, and methods of staging and monitoring the progress of disease by detecting cell death.

BACKGROUND OF THE INVENTION

Apoptosis and exposure of phosphatidylserine on the cell surface is a common feature of programmed cell death from species ranging from invertebrates such as *C. elegans* and *D. melanogaster* through vertebrate phyla to humans. The breakdown of the asymmetry of membrane phospholipids and increased exposure of phosphatidylserine on the cell surface leads to enhanced annexin V binding and provides a signal for phagocytosis by mononuclear cells. It has recently been reported that phosphatidylserine exposure during apoptosis reflects bi-directional trafficking of a particular subset of membrane vesicles between the cell surface and the cytoplasm.

Apoptosis is commonly characterized by condensation of nuclear chromatin, and fragmentation of nuclear structure into so-called apoptotic bodies. At present, there exists a variety of techniques that can detect the process of apoptosis at different stages. For example, the terminal stage of apoptosis can be assayed by morphological changes of the cell (such as the presence of apoptotic bodies). Before that, apoptosis can be assayed by DNA fragmentation using either gel analysis or the TUNEL technique. Earlier stages of apoptosis can be assayed by exposure of phosphatidylserine in the outer sheath of the membrane using an annexin V labelled protein, or by detecting the activation of caspase-3 using a fluorescent dye linking to a substrate peptide.

All of these techniques, however, have certain limitations. For example, gel analysis can only be applied to an extract of cells, not to a single cell or intact cells. The TUNEL method can only be applied to fixed cells, not living cells. annexin V can only detect events at the outer cell surface, not inside the cell. The caspase probe using a peptide linked fluorescence dye also has limitations. First, this probe cannot penetrate the cell membrane, and thus, it is typically used to assay cell extract. Secondly, the fluorescent change resulting from caspase cleavage involves mainly a shift of the emission spectrum in the dye rather than a total destruction of the fluorescence, and sensitivity is limited.

The most popular method for detecting apoptosis is the molecular recognition of surface-exposed phosphatidylserine that is based on the ability of annexin V to interact with phosphatidylserine exposed on the surface in a $Ca^{2+}$-dependent manner. Different variants of this method have been developed. For example, annexin V labelled with fluorescein has been used for flow cytometry, while annexin V labelled with red-near infrared dyes has been used for tissue imaging. This protein was also labelled with colloid gold for electron microscopy, with radioactive tracer for autoradiography on the tissue level and with peroxidase for histochemical studies. In all these tests, a high (up to 2.5 mM) extracellular concentration of $Ca^{2+}$ ions has to be provided for complete binding of annexin V to phosphatidylserine. For this reason, special buffers are required in order to detect surface phosphatidylserine. Furthermore, annexin V can associate with membrane surfaces containing by-products of lipid per oxidation that modify amines by producing negative charges, and detergents in the medium can also change the annexin V lipid binding specificity. In addition, routinely used cell harvesting techniques for adhering cells, such as trypsinization, can also produce false results in application of this method.

Thus, there remains a need for methods and compositions for the detection of cells undergoing cell death.

SUMMARY OF THE INVENTION

The present inventors have found that calcitonin receptor is a marker on cells undergoing cell death. The method of the present invention for detecting cell death using compounds that bind calcitonin receptor can be used on live cells, cells undergoing cell death and in a variety of buffers.

Accordingly, the present invention provides a method for detecting cell death in a cell, the method comprising:
i) contacting a cell with a compound that binds calcitonin receptor, and
ii) detecting the compound in or on the cell,
wherein the level of the compound in or on the cell is indicative of cell death.

The skilled person will readily be able to determine whether a level of the compound in or on the cell is indicative of cell death by comparison to the level of the compound in a reference sample or reference population of cells. To determine the reference level, the skilled person may include a suitable reference sample or reference population of cells as an experimental control. Alternatively, the level of the compound in or on the cell may be compared to known or predetermined reference levels.

Thus, in one embodiment, the method further comprises comparing the level of the compound in or on the cell with the level of the compound in or on a cell in a reference sample.

In another embodiment, the method comprises measuring the level of the compound in or on a population of cells and comparing the level of the compound to a reference level of the compound in or on a reference population of cells.

In one particular embodiment, the reference sample or reference population of cells comprises cells not undergoing cell death, and wherein the method comprises determining (a) there is a higher amount of cell death when the level of the compound is greater than the reference level, or (b) there is a lower amount of cell death when the level of the compound is less than the reference level.

In another embodiment, the reference sample or reference population of cells comprises cells undergoing cell death or cells treated to induce cell death.

In the methods of the invention, the skilled person may use any suitable compound that binds calcitonin receptor, including those already known in the art or those produced de novo using known techniques such as high-throughput chemical screens. In one embodiment, the compound that binds calcitonin receptor is a calcitonin-like ligand or an antibody. For example, the calcitonin-like ligand may be human calcitonin, salmon calcitonin, salmon calcitonin 8-32, calcitonin receptor stimulating peptide (CRSP), or amylin. In one particular embodiment, the calcitonin-like ligand comprises an amino acid sequence at least 80%, or at least 85%, or at least 87.5%, or at least 90%, or at least 95%, or at least 99% identical to any one of SEQ ID NOs:13 to 15. In another embodiment, the calcitonin-like ligand comprises a sequence identical to any one of SEQ ID NOs:13 to 15.

Techniques for detecting compounds that bind calcitonin receptor are known in the art. In one embodiment, the compound is detectably labelled. Any suitable detectable label known in the art may be used in the method of the invention, such as for example a fluorescent label or a radioactive label.

Antibodies that bind calcitonin receptor are commercially available and suitable for use in the methods of the invention. In one embodiment, the antibody binds an epitope of the calcitonin receptor comprising an amino acid sequence provided as any one of SEQ ID NOs:6 to 12.

In one embodiment, the methods of the invention are used to detect cell death, wherein the cell death is apoptosis, anoikis, autophagy or necrosis.

The methods of the invention may be used on a cell or cells in in vitro assays. The cells may be from, for example, a primary or secondary cultured cell line. Thus in one embodiment, the method is performed on a cell or population of cells in vitro.

In addition to cultured cells, the methods of the invention can be applied to cells derived from a subject. Thus, in one embodiment, the method is performed on cells obtained from a subject. The subject may be a mammal, for example a human or other primate, avian, fish or invertebrate. In one embodiment, the subject is a mammal selected from human or a mouse. In another embodiment, the subject is avian, such as poultry including a chicken. In yet another embodiment, the subject is a fish selected from salmon, trout and zebrafish. In yet another embodiment, the subject is an invertebrate selected from C. elegans and D. melanogaster. In yet another embodiment, the subject is a plant pest or animal pest. In one embodiment, the subject is an insect.

In another embodiment, the method comprises administering to a subject a compound that binds calcitonin receptor and determining the level of the compound in or on cells in a sample obtained from the subject, wherein the level of the compound is indicative of the level of cell death.

In one embodiment of the methods of the invention, the calcitonin receptor comprises an amino acid sequence at least 80% identical to any of SEQ ID NOs:1 to 5 or 52 to 54. In another embodiment, the calcitonin receptor comprises an amino acid sequence at least 85%, or at least 87.5%, or at least 90%, or at least 95% or at least 99% identical to any one of SEQ ID NOs:1 to 5 or 52 to 54. In another embodiment, the calcitonin receptor comprises an amino acid sequence identical to any one of SEQ ID NOs:1 to 5 or 52 to 54.

The present invention further provides a method of imaging cells undergoing cell death in a subject, the method comprising administering to the subject a compound that binds calcitonin receptor, allowing the compound to bind to cells within the subject, and determining the level of the compound within the subject.

In one embodiment, the subject is a mammal, avian, fish or invertebrate. In one embodiment, the subject is a mammal selected from a human and a mouse. In another embodiment, the subject is a primate. In another embodiment, the subject is avian, such as poultry including a chicken. In yet another embodiment, the subject is a fish selected from salmon, trout and zebrafish. In yet another embodiment, the subject is an invertebrate. In yet another embodiment, the subject is an insect. In one particular embodiment, the subject is selected from C. elegans and D. melanogaster.

The present invention further provides a method for determining the diagnosis, prognosis, and/or prediction of therapeutic outcome in a subject, the method comprising performing the method of the invention on a subject, a sample comprising cells obtained from a subject, or on cells obtained from the subject.

In one embodiment, the subject has or is suspected of having a condition associated with cell death. In one particular embodiment, the condition is selected from cancer; chemotherapy-induced cell death, radiation-induced cell death, or hormone-induced cell death in solid and hematological tumors; tumor resistance to therapy; acute cardiac allograft rejection; acute myocardial infarction; anthracycline-induced cardiotoxicity; arrhythmogenic right ventricle dysplasia; skeletal muscle cell death; congestive heart failure; coronary artery disease; atherosclerosis; infectious endocarditis; myocarditis; myocardial dysfunction; myocardial ischemia-reperfusion injury; non-cardiac allograft rejection; bacterial infection; viral infection; multiple organ dysfunction syndrome; septic shock; cerebral ischemia-reperfusion injury; macular degeneration; neurodegenerative disease; central nervous system trauma; autoimmune diabetes mellitus; rheumatoid arthritis; systemic lupus erythematosus; inflammatory bowel disease; multiple sclerosis; other autoimmune diseases; annexinopathies; osteoarthritis; renal failure; chronic renal atrophy and renal fibrosis; glomerular injury; and polycystic renal disease.

The present invention further provides a method of screening for a modulator of cell death, the method comprising:
  i) contacting a cell with a test agent,
  ii) contacting the cell with a compound that binds calcitonin receptor, and
  ii) detecting the level of the compound that binds calcitonin receptor in or on the cell.

In one embodiment, detection of a higher level of the compound that binds calcitonin receptor in or on the cell when compared to a reference cell is indicative of the agent being an inducer of cell death.

In another embodiment, the test agent is a candidate pesticide or insecticide and the cell is an animal pest cell or plant pest cell. In one particular embodiment, the cell is an insect cell.

In another embodiment, detection of a lower level of the compound that binds calcitonin receptor in or on the cell when compared to a reference cell is indicative of the agent being an inhibitor of cell death.

The present invention further provides a method for selectively delivering an agent to a cell undergoing cell death, the method comprising contacting a cell undergoing cell death with a compound that binds calcitonin receptor conjugated with the agent.

In one embodiment, the compound that binds calcitonin receptor is a calcitonin-like ligand or an antibody.

In another embodiment, the compound is detectably labelled.

The present invention further provides a compound that binds calcitonin receptor for the detection of cell death in a subject.

The present invention further provides use of a compound that binds calcitonin receptor in the preparation of a composition for detecting cell death in a subject.

In one embodiment, the compound that binds calcitonin receptor is a calcitonin-like ligand or an antibody.

In one embodiment of the method, the compound, or the use of the invention, the compound that binds calcitonin receptor is an antibody.

In one particular embodiment, the antibody comprises a variable heavy chain CDR3 comprising a sequence selected from SEQ ID NO:24, SEQ ID NO:32 or SEQ ID NO:40.

In another embodiment, the antibody comprises:
(a) CDR sequences of a variable heavy chain comprising
  i) CDR1 comprising a sequence selected from SEQ ID NO:22 and/or SEQ ID NO:25;
  ii) CDR2 comprising a sequence selected from SEQ ID NO:23 and/or SEQ ID NO:26;
  iii) CDR3 comprising SEQ ID NO:24, and/or
(b) CDR sequence of a variable light chain comprising
  i) CDR1 comprising a sequence provided as SEQ ID NO:27;
  ii) CDR2 comprising a sequence provided as SEQ ID NO:28; and/or
  iii) CDR3 comprising a sequence provided as SEQ ID NO:29.

In yet another embodiment, the antibody comprises:
(a) CDR sequences of a variable heavy chain comprising
  i) CDR1 comprising a sequence selected from SEQ ID NO:30 and/or SEQ ID NO:33;
  ii) CDR2 comprising a sequence selected from SEQ ID NO:31 and/or SEQ ID NO:34;
  iii) CDR3 comprising SEQ ID NO:32, and/or
(b) CDR sequence of a variable light chain comprising
  i) CDR1 comprising a sequence provided as SEQ ID NO:35;
  ii) CDR2 comprising a sequence provided as SEQ ID NO:36; and/or
  iii) CDR3 comprising a sequence provided as SEQ ID NO:37.

In another embodiment, the antibody comprises:
(a) CDR sequences of a variable heavy chain comprising
  i) CDR1 comprising a sequence selected from SEQ ID NO:38 and/or SEQ ID NO:41;
  ii) CDR2 comprising a sequence selected from SEQ ID NO:39 and/or SEQ ID NO:42;
  iii) CDR3 comprising SEQ ID NO:40, and/or
(b) CDR sequence of a variable light chain comprising
  i) CDR1 comprising a sequence provided as SEQ ID NO:43;
  ii) CDR2 comprising a sequence provided as SEQ ID NO:44; and
  iii) CDR3 comprising a sequence provided as SEQ ID NO:45.

In one embodiment, the antibody comprises a variable heavy chain comprising a sequence at least 99% identical to any one of SEQ ID NO:46, SEQ ID NO:48 or SEQ ID NO:50. In one particular embodiment, the sequence is identical to any one of SEQ ID NO:46, SEQ ID NO:48 or SEQ ID NO:50.

In yet another embodiment, the antibody comprises a variable light chain comprising a sequence at least 99% identical to any one of SEQ ID NO:47, SEQ ID NO:49 or SEQ ID NO:51. In one particular embodiment, the sequence is identical to any one of SEQ ID NO:47, SEQ ID NO:49 or SEQ ID NO:51.

In another embodiment, the antibody is produced by the hybridoma 9B4 as deposited with the European Collection of Cell Cultures (ECACC) under Deposit Reference 07081001.

The present invention further provides antibodies that bind calcitonin receptor. In one embodiment, the antibody comprises a variable heavy chain CDR3 comprising a sequence selected from SEQ ID NO:24, SEQ ID NO:32 or SEQ ID NO:40.

In another embodiment, the antibody comprises:
(a) CDR sequences of a variable heavy chain comprising
  i) CDR1 comprising a sequence selected from SEQ ID NO:22 and/or SEQ ID NO:25;
  ii) CDR2 comprising a sequence selected from SEQ ID NO:23 and/or SEQ ID NO:26;
  iii) CDR3 comprising SEQ ID NO:24, and/or
(b) CDR sequence of a variable light chain comprising
  i) CDR1 comprising a sequence provided as SEQ ID NO:27;
  ii) CDR2 comprising a sequence provided as SEQ ID NO:28; and/or
  iii) CDR3 comprising a sequence provided as SEQ ID NO:29.

In yet another embodiment, the antibody comprises:
(a) CDR sequences of a variable heavy chain comprising
  i) CDR1 comprising a sequence selected from SEQ ID NO:30 and/or SEQ ID NO:33;
  ii) CDR2 comprising a sequence selected from SEQ ID NO:31 and/or SEQ ID NO:34;
  iii) CDR3 comprising SEQ ID NO:32, and/or
(b) CDR sequence of a variable light chain comprising
  i) CDR1 comprising a sequence provided as SEQ ID NO:35;
  ii) CDR2 comprising a sequence provided as SEQ ID NO:36; and/or
  iii) CDR3 comprising a sequence provided as SEQ ID NO:37.

In another embodiment, the antibody comprises a variable heavy chain comprising a sequence at least 99% identical to SEQ ID NO:46 or SEQ ID NO:48. In one particular embodiment, the sequence is identical to SEQ ID NO:46 or SEQ ID NO:48.

In yet another embodiment, the antibody comprises a variable light chain comprising a sequence at least 99% identical to SEQ ID NO:47 or SEQ ID NO:49. In one particular embodiment, the sequence is identical to SEQ ID NO:47 or SEQ ID NO:49.

The present invention further provides an antibody conjugate comprising the antibody of the invention, wherein the antibody conjugate further comprises an imaging agent. The imaging may be selected from, for example, a radiolabel, an enzyme, a fluorescent label, a luminescent label, a bioluminescent label, a magnetic label and/or biotin.

The present invention further provides an isolated polynucleotide encoding the antibody of the invention.

In one embodiment, the polynucleotide comprises a sequence of nucleotides selected from any one of SEQ ID Nos:22 to 37, 46, 47, 48 and/or 49.

In one embodiment of the methods of the invention, the cell that is contacted with the compound that binds calcitonin receptor is not a leukemia cell.

In another embodiment of the methods of the invention, the cell that is contacted with the compound that binds calcitonin receptor is not a brain tumor cell.

In yet another embodiment of the methods of the invention, the subject does not have or is not suspected of having leukemia.

In yet another embodiment of the methods of the invention, the subject does not have or is not suspected of having a brain tumor.

In yet another embodiment, the present invention provides a method of screening for a pesticide or insecticide that causes cell death in a plant pest or animal pest, the method comprising:

a) contacting the plant pest or animal pest, or cells of the plant pest or animal pest, with a candidate pesticide or insecticide, b) contacting the plant pest or animal pest, or cells of the plant pest or animal pest, with a compound that binds calcitonin receptor, and c) detecting the compound in or on the plant pest or animal pest, or in or on cells of the plant pest or animal pest.

In one embodiment, the calcitonin receptor comprises a sequence at least 80% identical to any one of SEQ ID Nos:52 to 54. In another embodiment, the calcitonin receptor comprises a sequence at least 85%, at least 90%, at least 95%, at least 98%, at least 99%, or 100% identical to any one of SEQ ID Nos:52 to 54

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. MG 63 cells were treated with 1 μM staurosporine for 19 hours in several experiments. (a) A representative composite image at high magnification (×63; DAPI; annexin V, and MAb 2C4:AF568 staining) (b) is similar but at lower magnification (×20). Both (a, b) represent live staining with MAb 2C4:AF568. (c) A further composite image from a separate experiment is shown with magnification (×40). The separated images are shown (d) DAPI, nuclear stain, (e) annexin V, plasma membrane, (f) cleaved caspase 3 and (g) MAb 2C4:AF568. (h) Representative composite image of live staining with MAb 9E10:AF647 (IgG1 isotype control) and annexin V. (i [magnification ×20], j [magnification ×63]) The results of staining with MAb 2C4:AF568 after fixation. (k) Representative composite image stained for cleaved caspase 8, annexin V with live staining using MAb 2C4:AF568. (l) Representative composite image stained for cleaved caspase 9, annexin V with live staining using MAb 2C4:AF568. (m-q) The results of co-staining with two anti-CTR antibodies are shown: (m), composite image; (n), DAPI; (o), cleaved caspase 3; (p), anti-hCTR MAb 2C4: AF568; (q), anti-hCTR MAb 1H10:biotin. All panels represent live staining with 10 μg/mL MAb 2C4:AF568 except (h) live staining with 10 μg/mL MAb 9E10:AF647 and (i, j) in which staining was performed with MAb 2C4:AF568 post-fixation.

Figure 2:
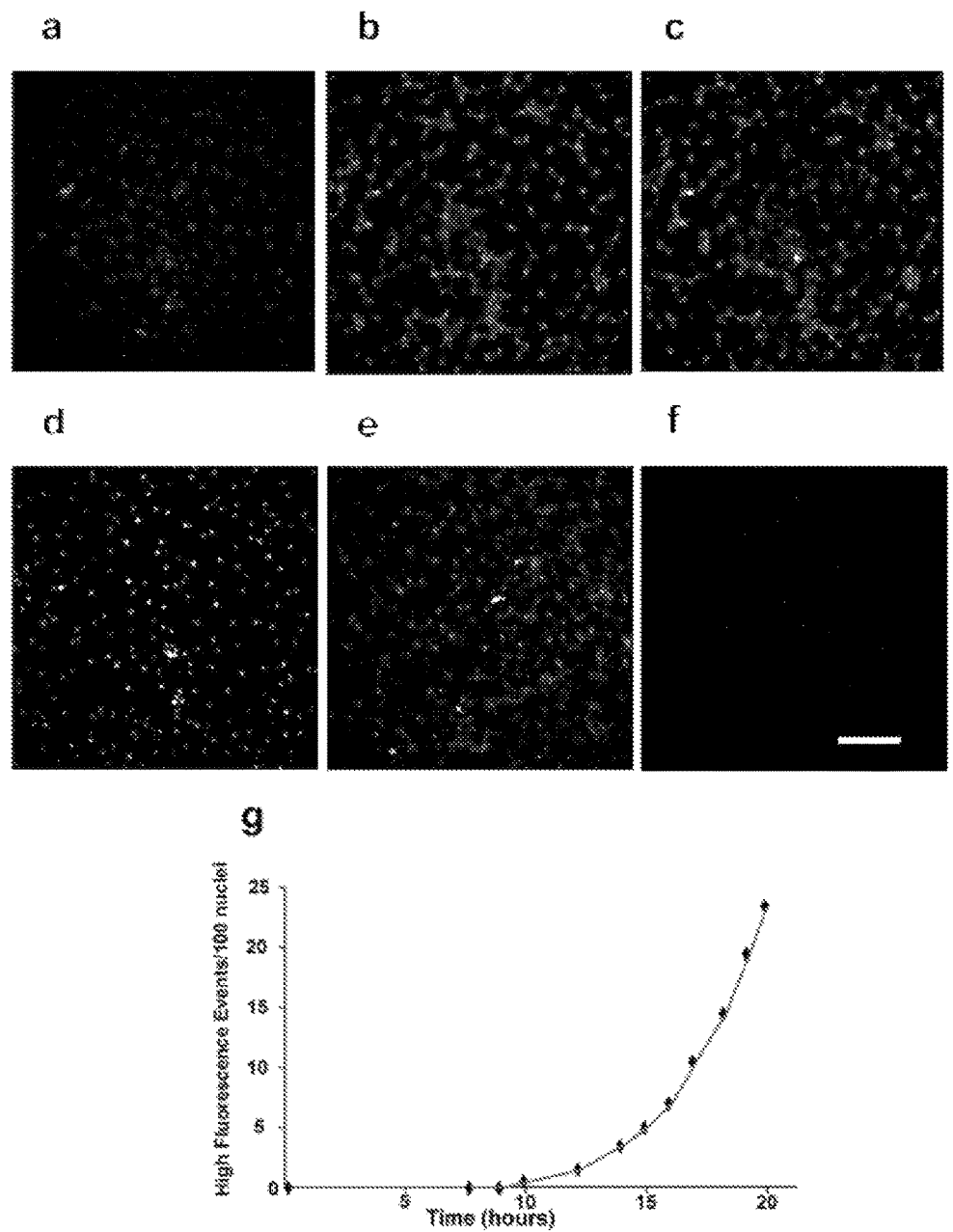

FIG. 2. Quantitative analysis of MAb 2C4:AF568 positive MG63 cells was performed using an InCell Analyzer 2000. Images of the field for quantification after treatment with 1 μM staurosporine and addition of 30 ng/mL MAb 2C4:AF568 both added at zero time (showing nuclei and MAb 2C4:AF568 fluorescence). (a) 0 hours, (b) 5 hours, (c) 7 hours, (d) 20 hours, (e) 20 hours without staurosporine, (f) 20 hours with the isotype control MAb 9E10:AF647 and staurosporine. (g) The rise in the number of high fluorescence was quantified and expressed as events per 100 nuclei.

Figure 3:
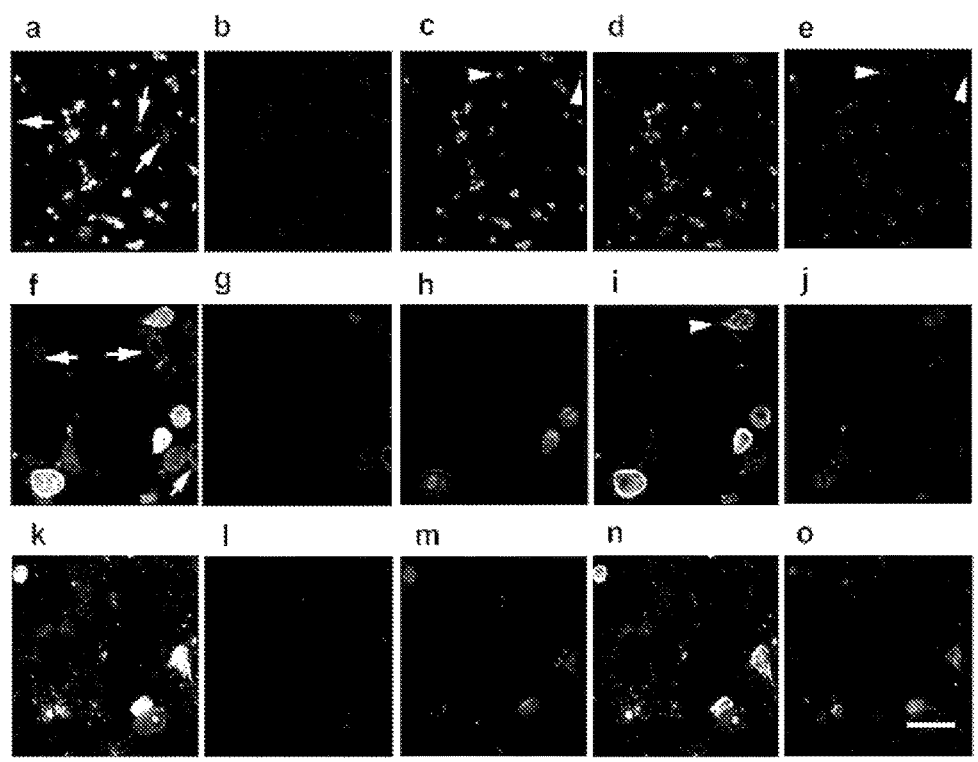

FIG. 3. (a-e) GBM-L2 cells treated with 1 μM staurosporine for 19 hours. (a) Representative composite image of (b) DAPI [nuclear stain], (c) MAb 2C4:AF568, (d) annexin V and (e) caspase 3. (f-j) A172 cells treated with 1 μM staurosporine for 19 hours. (f) Representative composite image of (g) DAPI [nuclear stain], (h) MAb 2C4:AF568, (i) annexin V and (j) caspase 3. (k-o) COS-7 cells treated with 1 μM staurosporine for 19 hours. (k) Representative composite image of (l) DAPI [nuclear stain], (m) MAb 2C4: AF568, (n) annexin V and (o) caspase 3.

Figure 4:
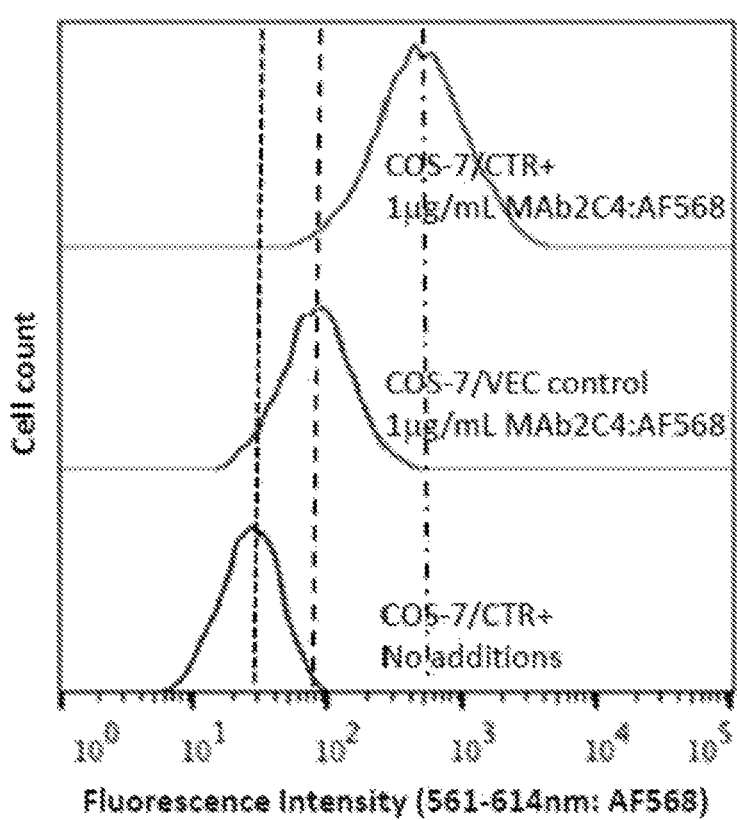

FIG. 4. FACS of COS-7/CTR+ cells with expression of human calcitonin receptor (hCTR) and vector control (COS-7/VEC). The live staining was blocked with 5% BSA.

Figure 5:
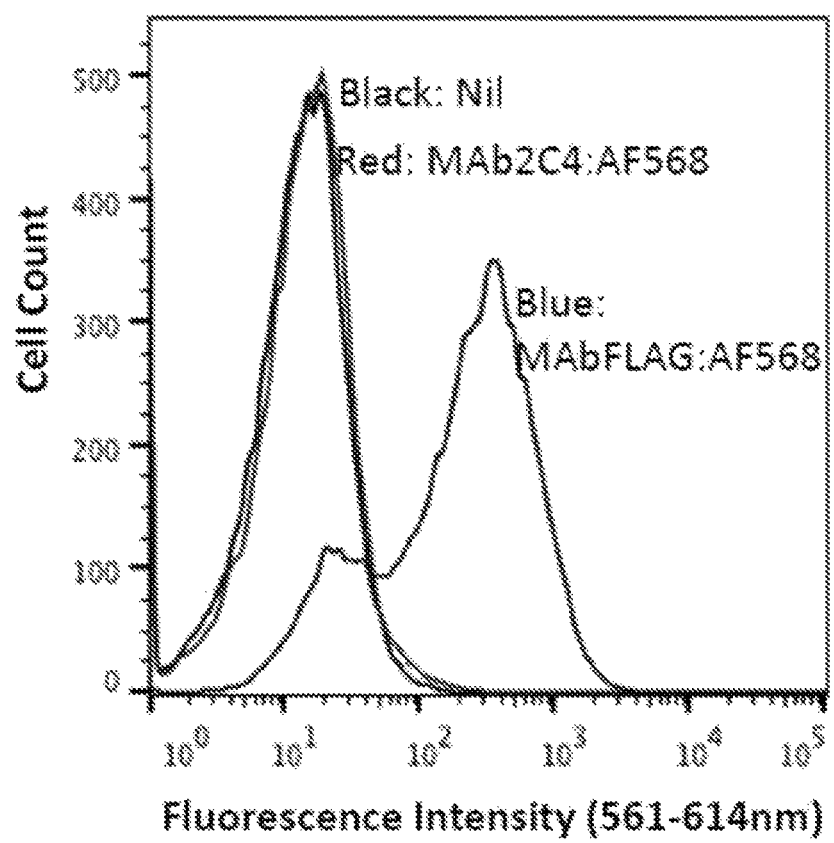

FIG. 5. Validation of the isotype IgG1 negative control anti-FLAG:AF568 antibody conjugate (MAbFLAG: AF568). The rightwards shift in fluorescence intensity (FI) indicates binding to the surface of the HEK293/PAReceptor-FLAG stable transfectant cell line. This demonstrates the validity of the MAbFLAG:AF568 antibody used as a negative IgG1 isotype control in subsequent figures.

Figure 6:
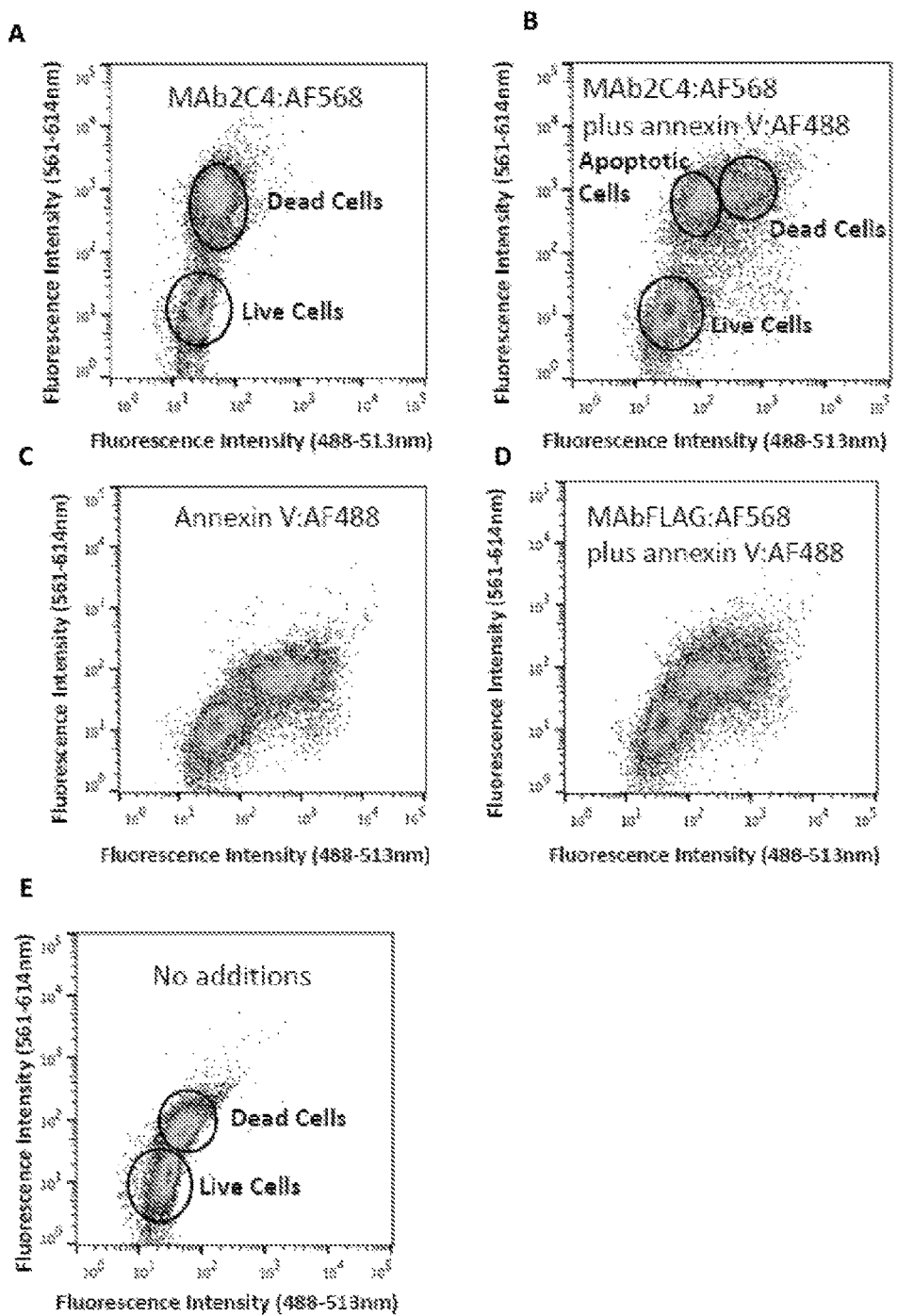

FIG. 6. Scatter plots from FACS analysis of Jurkat cells treated with the cytotoxin staurosporine (5×10-7M) for 40 hours to induce Programmed Cell Death including apoptosis and finally cell death (necrosis). The populations of live, apoptotic and dead cells were live-stained with 1 μg/mL MAb2C4:AF568 and/or annexin V:AF488 and the fluorescence intensity (FI) of each shown on the ordinate and abscissa respectively. A: Cell populations stained with MAb2C4:AF568 alone; B: Cell populations stained with MAb2C4:AF568 plus annexin V:AF488; C: Cell populations stained with annexin V:AF488 alone; D: Cell populations stained with MAbFLAG:AF568 plus annexin V:AF488; E: No additions. The results show increased FI with MAb2C4:AF568 [A & B], whereas there is no change in FI with MAbFLAG:AF568 [D], the IgG1 isotype control.

Figure 7:
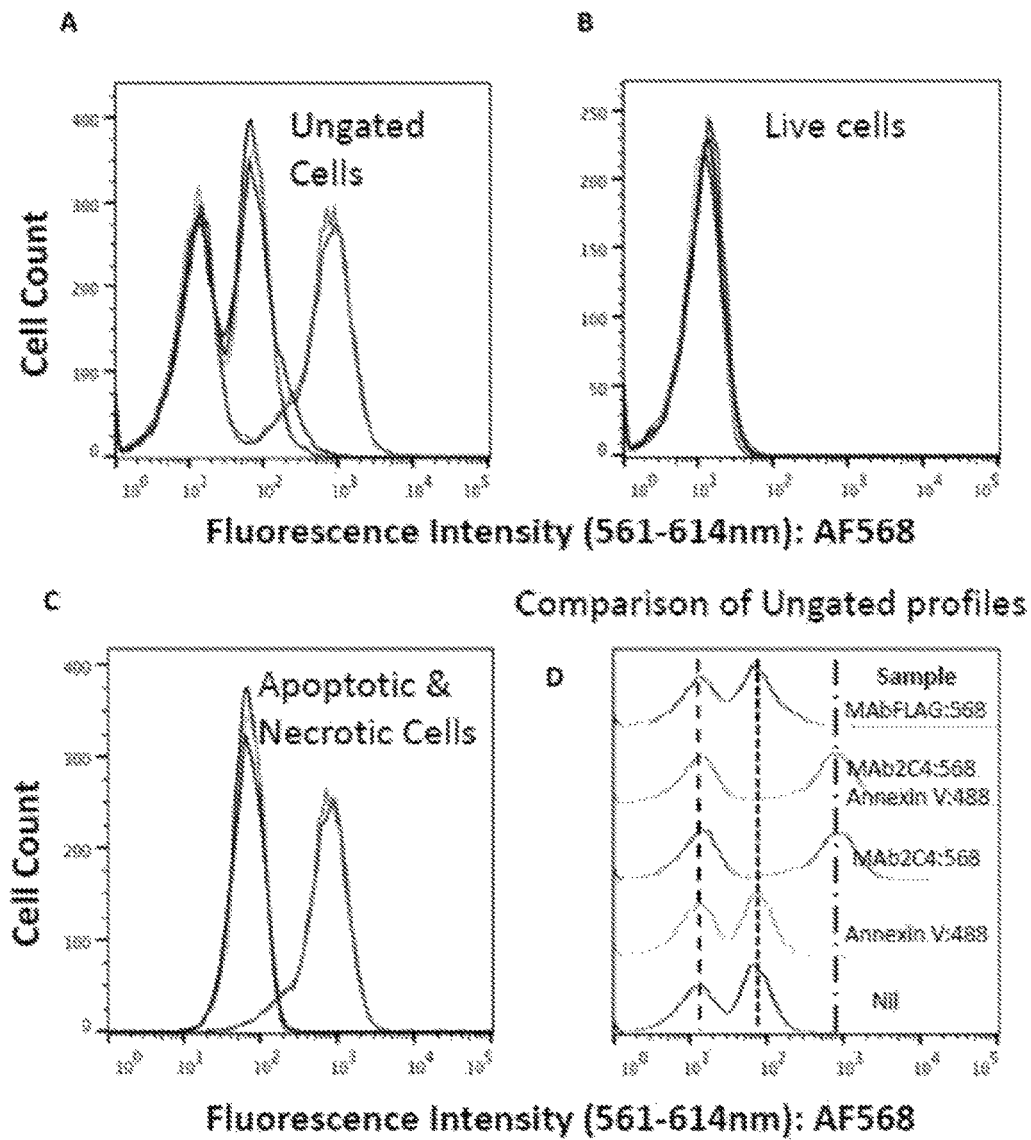

FIG. 7. Histograms from FACS analysis of Jurkat cells induced to undergo Programmed Cell Death [PCD] (as for FIG. 6). Shown are overlaid curves representative of live, apoptotic and necrotic (dead) cell populations [A, B & C]. In D these curves are aligned for ease of comparison. The results show MAb2C4:AF568 binding results in an increase in FI (red channel) of apoptotic and dead cell populations, compared to the MAbFLAG:AF568 isotype control.

Figure 8:
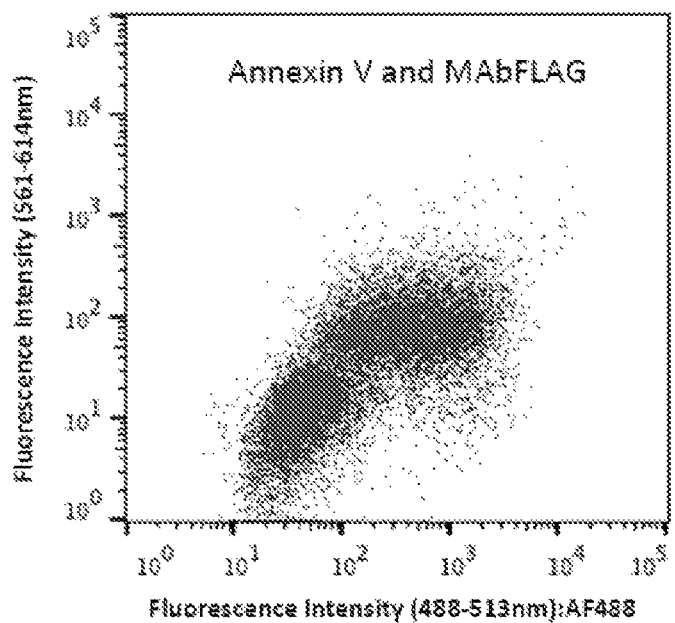
Figure 8:
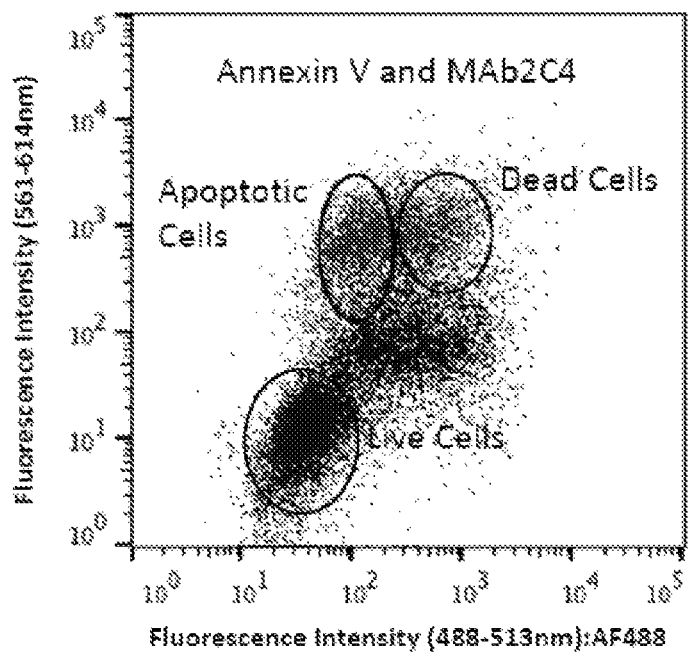

FIG. 8. Overlaid scatter plots showing increasing FI of apoptotic and dead Jurkat populations stained with MAb2C4:AF568 compared to the MAbFLAG:AF568 isotype control.

Figure 9:
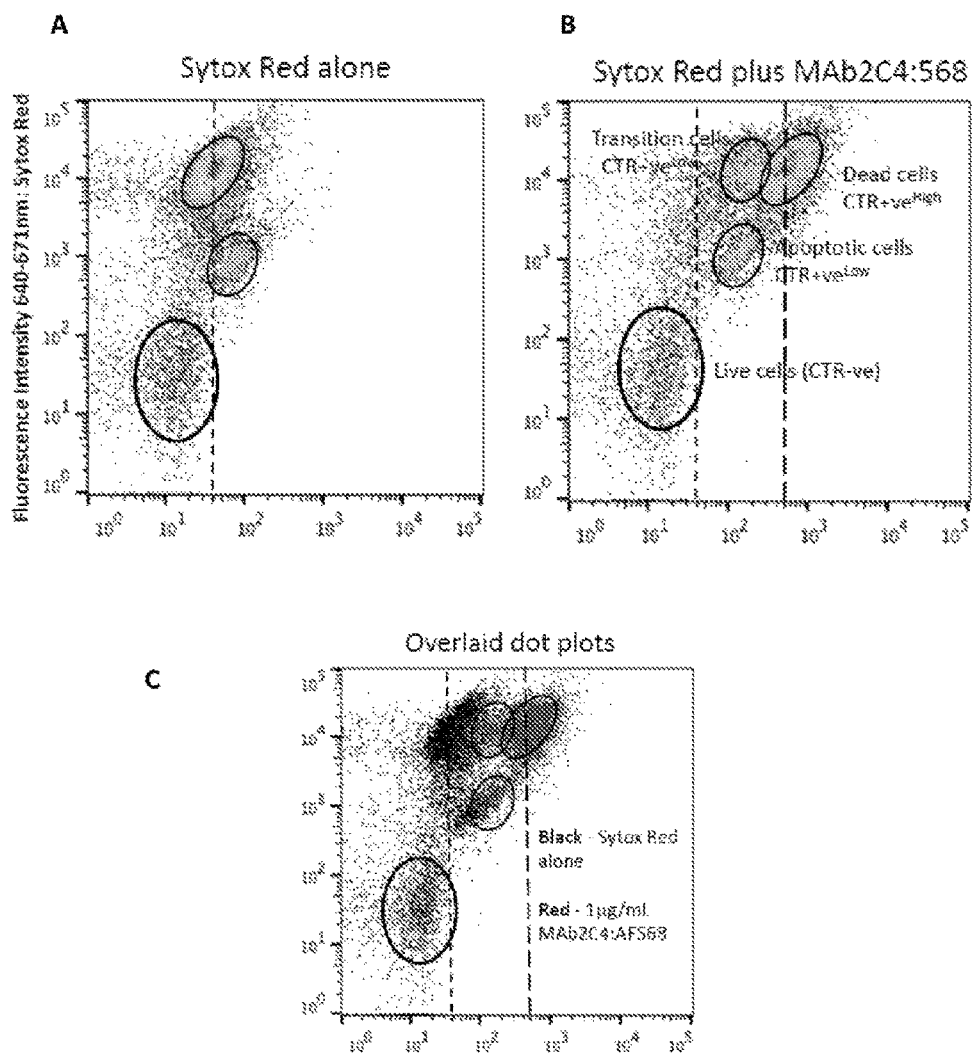

FIG. 9. Scatter plots showing FI with MAb2C4:AF568 (abscissa) and/or Sytox Red (ordinate). A: Sytox Red alone; B: Increased FI of apoptotic, transition and dead (necrotic) cell populations stained with MAb2C4:AF568; C: Overlaid dot plots of A & B.

Figure 10:
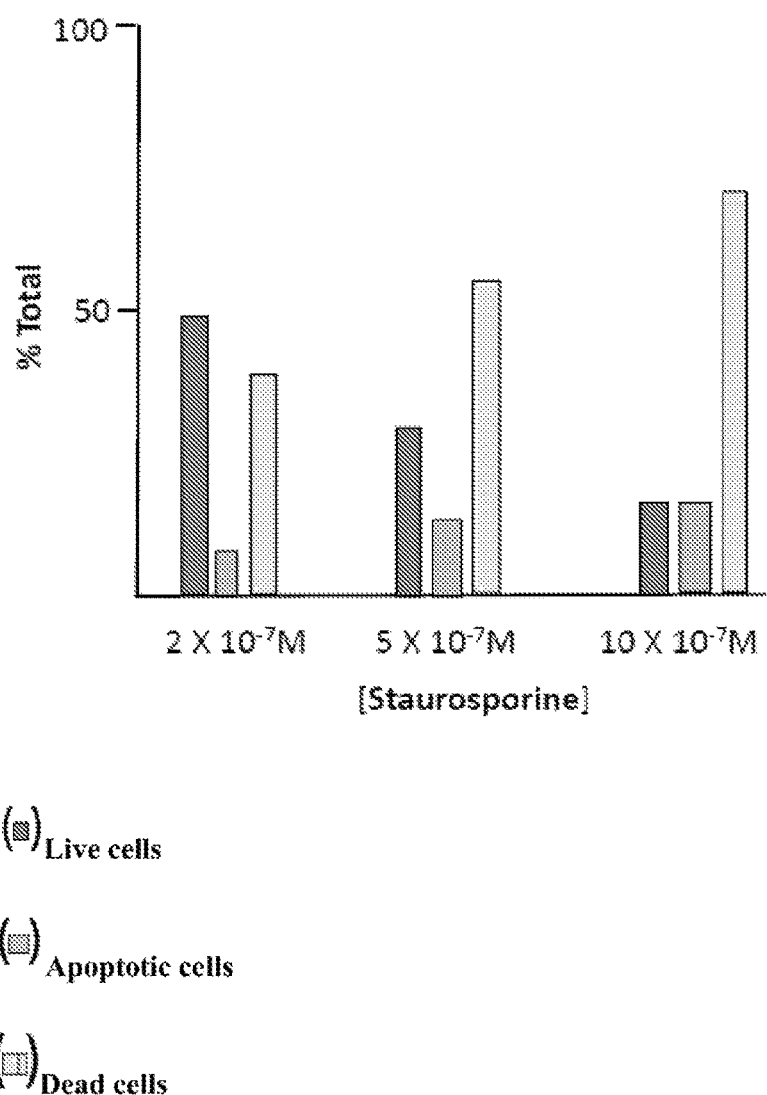

FIG. 10. Analysis of relative proportions of live, apoptotic and dead Jurkat cells challenged with $2\times10^{-7}$M, $5\times10^{-7}$M and $10\times10^{-7}$M staurosporine for 40 hours. The proportion of live cells decreases with increasing concentrations of the cytotoxin. The proportion of apoptotic and dead cell populations increases as determined by Sytox Red and MAb2C4: AF568 staining.

KEY TO THE SEQUENCE LISTING

SEQ ID NO:1—Amino acid sequence of human calcitonin receptor.

SEQ ID NO:2—Amino acid sequence of mouse calcitonin receptor.

SEQ ID NO:3—Amino acid sequence of chicken calcitonin receptor.

SEQ ID NO:4—Amino acid sequence of fish calcitonin receptor.

SEQ ID NO:5—Amino acid sequence of *C. elegans* calcitonin receptor.

SEQ ID NO:6—Amino acid sequence of epitope of human calcitonin receptor.

SEQ ID NO:7—Amino acid sequence of epitope of mouse calcitonin receptor.

SEQ ID NO:8—Amino acid sequence of epitope of chicken calcitonin receptor.

SEQ ID NOs:9 to 11—Amino acid sequence of epitopes of fish calcitonin receptor.

SEQ ID NO:12—Amino acid sequence of epitope of *C. elegans* calcitonin receptor.

SEQ ID NO:13—Amino acid sequence of human calcitonin

SEQ ID NO:14—Amino acid sequence of salmon calcitonin

SEQ ID NO:15—Amin acid sequence of salmon calcitonin 8-32.

SEQ ID NO:16—2C4 VH sequence.

SEQ ID NO:17—6G11/1D10 VH sequence.

SEQ ID NO:18—9B4 VH sequence.

SEQ ID NO:19—2C4 VL sequence.

SEQ ID NO:20—6G11/1D10 VL sequence.

SEQ ID NO:21—9B4 VL sequence.

SEQ ID NO:22—2C4 CDR H1 Chothia/AbM

SEQ ID NO:23—2C4 CDR H2 Chothia/AbM

SEQ ID NO:24—2C4 CDR H3 Chothia/AbM

SEQ ID NO:25—2C4 CDR H1 Kabat

SEQ ID NO:26—2C4 CDR H2 Kabat

SEQ ID NO:27—2C4 CDR L1

SEQ ID NO:28—2C4 CDR L2

SEQ ID NO:29—2C4 CDR L3

SEQ ID NO:30—6G11/1D10 CDR H1 Chothia/AbM

SEQ ID NO:31—6G11/1D10 CDR H2 Chothia/AbM

SEQ ID NO:32—6G11/1D10 CDR H3 Chothia/AbM

SEQ ID NO:33—6G11/1D10 CDR H1 Kabat

SEQ ID NO:34—6G11/1G10 CDR H2 Kabat

SEQ ID NO:35—6G11/1G10 CDR L1

SEQ ID NO:36—6G11/1D10 CDR L2

SEQ ID NO:37—6G11/1D10 CDR L3

SEQ ID NO:38—9B4 CDR H1 Chothia/AbM

SEQ ID NO:39—9B4 CDR H2 Chothia/AbM

SEQ ID NO:40—9B4 CDR H3 Chothia/AbM

SEQ ID NO:41—9B4 CDR H1 Kabat

SEQ ID NO:42—9B4 CDR H2 Kabat

SEQ ID NO:43—9B4 CDR L1

SEQ ID NO:44—9B4 CDR L2

SEQ ID NO:45—9B4 CDR L3

SEQ ID NO:46—2C4 VH nucleotide sequence

SEQ ID NO:47—2C4 VL nucleotide sequence

SEQ ID NO:48—6G11/10D1 VH nucleotide sequence

SEQ ID NO:49—6G11/10D1 VL nucleotide sequence

SEQ ID NO:50—9B4 VH nucleotide sequence

SEQ ID NO:51—9B4 VL nucleotide sequence

SEQ ID NO:52—Mosquito calcitonin receptor

SEQ ID NO:53—Mosquito calcitonin receptor

SEQ ID NO:54—tack calcitonin receptor

DETAILED DESCRIPTION OF THE INVENTION

Deposit Under the Budapest Treaty

The hybridoma designated 9B4 was deposited on 10 Aug. 2007 with the European Collection of Cell Cultures (ECACC) under Deposit Reference 07081001.

This deposit was made under the provisions of the Budapest Treaty on the International Recognition of the Deposit of Microorganisms for the Purpose of Patent Procedure and the Regulations thereunder. This assures maintenance of viable cultures for 30 years from the date of the deposit. The organism will be made available by the ECACC under the terms of the Budapest Treaty which assures permanent and unrestricted availability of the progeny of the culture to the public upon issuance of the pertinent patent. Availability of a deposited strain is not to be construed as a license to practice the invention in contravention of the rights granted under the authority of any government in accordance with its patent laws.

General Techniques and Definitions

Unless specifically defined otherwise, all technical and scientific terms used herein shall be taken to have the same meaning as commonly understood by one of ordinary skill in the art (e.g., in protein chemistry, biochemistry, cell culture, molecular genetics, microbiology, immunology, medical imaging and immunohistochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, 3$^{rd}$ edn, Cold Spring Harbour Laboratory Press (2001), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term "subject" refers to an animal such as a mammal, e.g. humans or non-human mammals such as a, primate, mouse, cats, dogs, cattle, sheep, horses, rabbits and monkeys, or to an avian such as poultry including chickens, fish such as salmon, trout and zebrafish, and an invertebrate, such as for example, *C. elegans* or an insect, such as but not limited to *D. melanogaster*. In one embodiment, the subject is a primate. In another embodiment, the subject is human.

The "sample" may be of any suitable type and may refer, for example, to a material comprising cells suspected of undergoing cell death. The sample can be used as obtained directly from the source or following at least one step of (partial) purification. The sample can be prepared in any convenient medium which does not interfere with the method of the invention. Typically, the sample comprises cells or tissues and/or is an aqueous solution or biological fluid comprising cells or tissue. Pre-treatment may involve, for example, diluting viscous fluids, and the like. Treatment of a sample can involve filtration, distillation, separation, concentration, inactivation of interfering components, and the addition of reagents. The selection and pre-treatment of biological samples prior to testing is well known in the art and need not be described further.

As used herein, the term "epitope" refers to a region of calcitonin receptor as described herein which may be bound by an antibody.

As used herein "binds an epitope" means that an antibody need only bind within the given amino acid sequence, and need not bind the entire amino acid sequence.

An "isolated antibody", as used herein, refers to an antibody that is substantially free of other antibodies having different antigenic specificities (e.g., an isolated antibody that specifically binds CTR is substantially free of antibodies that specifically bind antigens other than CTR). Moreover, an isolated antibody may be substantially free of other cellular material. "Administering" as used herein is to be construed broadly and includes administering a compound as described herein to a subject as well as providing a compound as described herein to a cell.

Detecting Cell Death

Cell death is a feature of many diseases as well as therapeutic methods, for example in the treatment of cancer. It is therefore desirable to be able to measure cell death, to assess either the status of a disease that involves cell death or the effect of a treatment that induces cell death. As used herein, the term "cell death" includes reference to forms of programmed cell death, such as apoptosis, anoikis, and autophagy, as well as reference to necrosis.

Apoptosis is the term used to describe a type of cellular death that occurs in many tissues as a normal physiological process. This form of cell death involves activation of a built-in genetic program for cell suicide by which cells essentially autodigest. Remnants of the dead cells are then cleared by neighbouring phagocytic cells, without resulting in inflammation or scarring. Apoptosis thus stands in contrast to cell death caused, for example, by oxygen-deprivation in the settings of myocardial infarction or stroke, where cells lose their energy supplies, rupture and spill their contents into the extracellular milieu. This type of cell death, known as necrosis, often results in inflammation.

Apoptosis plays a role in many normal processes including tissue turnover, proper development and maintenance of the immune system, development of the nervous system, and elimination of virus-infected cells. It is a well-ordered process that is characterized by DNA fragmentation, chromatin condensation, membrane blebbing and cell shrinkage. Cells undergoing apoptosis ultimately disassemble into membrane-enclosed vesicles (apoptotic bodies) that are engulfed by neighbouring cells and phagocytes, thus preventing an inflammatory response.

In contrast to the role of apoptosis in normal cellular processes, aberrantly regulated apoptotic cell death can lead to a variety of disease states and pathological conditions. As an example, dysregulation of apoptosis in the nervous system can result in unintended neuronal cell death which contributes to neurodegenerative diseases such as Alzheimer's disease, Parkinson's disease and amyotrophic lateral sclerosis (ALS). Additionally, viral infection can cause apoptosis such as T-cell apoptosis induced by the human immunodeficiency virus (HIV). The failure of normal apoptosis also can lead to disease, as in the case of autoimmune diseases in which immune cells that normally would have been eliminated through apoptosis attack normal tissues. Suppression of apoptosis can also contribute to tumorigenesis.

Integrin-mediated cell attachment is one regulator of apoptosis. Most types of normal cells are anchorage-dependent; in these cells, the loss of integrin-mediated cell attachment to the extracellular matrix results in a subtype of apoptosis known as "anoikis". Integrins suppress anoikis in attached cells by activating signalling pathways that promote survival and by inactivating pathways that promote apoptosis.

Autopohagy is one form of programmed cell death that is induced in response to starvation or stress, causing the formation of double membrane vesicles called autophagosomes that engulf proteins and organelles. Autophagosomes then fuse with lysosomes where the autophagosome and their cargo are degraded. This lysosome-mediated cellular self-digestion serves to recycle intracellular nutrients to sustain cell metabolism during starvation and to eliminate damaged proteins and organelles that accumulate during stress. Autophagy dysfunction is a major contributor to diseases including, but not limited to, neurodegeneration, liver disease, and cancer. Many human neurodegenerative diseases are associated with aberrant mutant and/or polyubiquitinated protein accumulation and excessive neuronal cell death.

Necrosis, which is also known as accidental cell death, is typically induced by any of a variety of sudden, severe, non-physiological insults, for example physical, chemical, and ischemic insults. The process is generally characterized by progressive cell swelling, denaturation and coagulation of cytoplasmic proteins, disintegration of subcellular organelles and irreversible collapse of the plasma membrane integrity. This latter feature permits leakage of cytotoxic and other cellular components, inducing a local inflammatory response. Loss of membrane integrity, a feature common to both apoptosis and necrosis, allows intracellular components to leak out of cells. As such, serum and plasma levels of intracellular components have been used as surrogate markers of cell death.

The present inventors have found that contacting a cell undergoing cell death with a compound that binds calcitonin receptor, and detecting the compound in or on the cell, results in a high intensity signal above background when compared to cells not undergoing cell death. Accordingly, the methods of the present invention can be used, for example, for detecting cell death in cultured cells or in in vitro cell samples, or can be used for imaging cells undergoing cell death in vivo, for screening for modulators of cell death, and for selectively delivering an agent to a cell undergoing cell death.

Compounds that Bind Calcitonin Receptor

The calcitonin receptor belongs to the Family B seven transmembrane domain G-protein-coupled receptors. Porcine calcitonin receptor was the first to be cloned (Lin et al., 1991). Shortly afterwards, the human, and several other species, of calcitonin receptor were cloned and characterised (Goldring et al. 1993). The amino acid sequence of human calcitonin receptor is provided as SEQ ID NO:1. The physiological function of the thyrocalcitonin (CT)/receptor (CTR) complex has been previously described in terms of a homeostatic mechanism for calcium, which was active under conditions of hypercalcaemia (Hirsch and Baruch, 2003).

Reference to calcitonin receptor as used herein includes isoforms, splice variants and allelic variants of calcitonin receptor as would be understood by one skilled in the art (see, for example, Gorn et al., 1995; Nakamura et al., 1997; Masi et al., 1998).

The present inventors have now shown that the calcitonin receptor (CTR) is expressed by cells undergoing cell death and can be detected at levels greater than seen in cells that are not undergoing cell death. Thus, compounds that bind to CTR will, by way of non-limiting example, be useful for methods of detecting cells undergoing cell death, for the screening of modulators of cell death (for example, inducers or inhibitors of apoptosis or anoikis), and for diagnosing, prognosing, predicting, or staging of disease or monitoring the progress of cell death and/or disease.

Compounds that bind CTR that are useful in the present invention may be any compound, e.g. a polypeptide, ligand or other molecule, identified as having binding affinity to CTR. The binding between a compound and CTR may be mediated by covalent or non-covalent interactions or a combination of covalent and non-covalent interactions. When the interaction of the compound and CTR produces a non-covalently bound complex, the binding which occurs is typically electrostatic, hydrogen-bonding, or the result of hydrophilic/lipophilic interactions. Particularly preferred compounds that bind CTR are anti-CTR antibodies and calcitonin-like ligands.

Although not essential, the compound may bind specifically to CTR. The phrase "bind specifically," means that under particular conditions, the compound binds CTR and does not bind to a significant amount to other, for example, proteins or carbohydrates. Specific binding to CTR under such conditions may require an antibody that is selected for its specificity. A variety of immunoassay formats may be used to select antibodies specifically immunoreactive with CTR. For example, solid-phase ELISA immunoassays are routinely used to select antibodies specifically immunoreactive with a protein or carbohydrate. See Harlow and Lane (1988) Antibodies, a Laboratory Manual, Cold Spring Harbor Publications, New York, for a description of immunoassay formats and conditions that can be used to determine specific immunoreactivity.

The skilled person will understand that the antibodies and calcitonin-like ligands suitable for use in the methods of the present invention can be readily conjugated to detectable labels using known methods. As understood in the art a conjugate is a molecule or complex formed by linking a molecule to at least one other molecule or other moiety. The conjugate is preferably stable under physiological conditions, i.e., the linked components remain linked together under physiological conditions. The linkage can be any suitable chemical or physicochemical linkage, including a covalent bond and a noncovalent bond. Conjugates include recombinant fusion proteins. The linkage between any two components of the conjugate can be direct, i.e., without a linker moiety, or it can be indirect, i.e., it can include a linker moiety connecting the two components. In one non-limiting example, the linkage involves a biotin-streptavidin interaction.

Calcitonin Receptor Ligands

In some embodiments of the methods of the present invention, the compound that binds calcitonin receptor may be a calcitonin-like ligand. As used herein, the term "calcitonin-like ligand" refers to human calcitonin (SEQ ID NO:13), salmon calcitonin (SEQ ID NO:14), salmon calcitonin 8-32 (SEQ ID NO:15), calcitonin receptor stimulating peptide (CRSP), amylin, and other calcitonin receptor binding ligands or related molecules as known in the art. Calcitonin is a polypeptide hormone of 32 amino acids, with a molecular weight of 3454.93 Daltons for the human form. Together with the other aforementioned calcitonin-like ligands, with the exception of salmon calcitonin 8-32, this group of peptides shares a conserved tertiary structure with an N-terminal disulfide-bridged ring.

As would be understood by the person skilled in the art, non-peptide analogs of calcitonin-like ligands are useful in the methods of the present invention. Thus, the term "calcitonin-like ligand" also encompasses peptide mimetics and peptide analogs. The terms "mimetic", "peptidomimetic" and "mimic" as used herein refer to a synthetic chemical compound that has substantially the same structural and/or functional characteristics of the peptides. The mimetic can be entirely composed of synthetic, non-natural analogues of amino acids, or, may be a chimeric molecule of partly natural amino acid residues and partly non-natural analogs of amino acids.

A peptide may be characterized as a mimetic when all or some of its residues are joined by chemical means other than natural peptide bonds. Individual mimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, but not limited to, ketomethylene (e.g., $-C(=O)-CH_2-$ for $-C(=O)-NH-$), aminomethylene ($CH_2-NH$), ethylene, olefin ($CH=CH$), ether ($CH_2-O$), thioether ($CH_2-S$), tetrazole ($CN_4-$), thiazole, retroamide, thioamide, or ester (see, e.g., Spatola (1983) In: Chemistry and Biochemistry of Amino Acids, Peptides and Proteins, Vol. 7, pp 267-357, "Peptide Backbone Modifications" Marcell Dekker, NY).

A mimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. Retro-inverso modification of naturally occurring peptides involves the synthetic assembly of amino acids with α-carbon stereochemistry opposite to that of the corresponding L-amino acids, i.e., D- or D-allo-amino acids in inverse order to the native peptide sequence. A retro-inverso analogue, thus, has reversed termini and reversed direction of peptide bonds, while essentially maintaining the topology of the side chains as in the native peptide sequence. One skilled in the art understands that these and other mimetics are encompassed within the meaning of the term "mimetic" as used herein.

Analogs of calcitonin-like ligands include small molecule analogs. The compounds may encompass numerous chemical classes though typically they are organic molecules, preferably small organic compounds. In one embodiment, a synthetic compound identified or designed by the methods of the invention has a molecular weight equal to or less than about 5000, 4000, 3000, 2000, 1000 or 500 Daltons. A compound suitable for use in the methods of the present invention is preferably soluble under physiological conditions.

Such compounds can comprise functional groups necessary for structural interaction with proteins, for example hydrogen bonding, and may include at least an amine, carbonyl, hydroxyl or carboxyl group, or at least two of the functional chemical groups. The compound may comprise cyclical carbon or heterocyclic structures and/or aromatic or polyaromatic structures substituted with one or more of the above functional groups. Small molecule analogs of calcitonin-like ligands are known in the art and include those described in Boros et al. (2005).

Antibodies

In some embodiments, the compound that binds calcitonin receptor is an antibody. The term "antibody" as used herein includes polyclonal antibodies, monoclonal antibodies, bispecific antibodies, diabodies, triabodies, heteroconjugate antibodies, chimeric antibodies, humanised or human antibodies including intact molecules as well as fragments thereof, antigen binding portions of antibodies and other antibody-like molecules. Antibodies include modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light (VL) and heavy chain (VH) variable regions which may be joined directly or through a linker, or Fd fragments containing the heavy chain variable region and the CH1 domain. An scFv consisting of the variable regions of the heavy and light chains linked together to form a single-chain antibody (Bird et al., 1988; Huston et al., 1988) and oligomers of scFv such as diabodies and triabodies are also encompassed by the term "antibody". Also encompassed are fragments of antibodies such as Fab, (Fab')2 and FabFc2 fragments which contain the variable regions and parts of the constant regions. Complementarity determining region (CDR)-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit or rat) or human origin or may be chimeric (Morrison et al., 1984) or humanized (Jones et al., 1986). As used herein the term "antibody" includes these various forms. Using the guidelines provided herein and those methods well known to those skilled in the art which are described in the references cited above and in such publications as Harlow & Lane, Antibodies: a Laboratory Manual, Cold Spring Harbor Laboratory, (1988) the antibodies for use in the methods of the present invention can be readily made.

The antibodies may be Fv regions comprising a variable light (VL) and a variable heavy (VH) chain in which the light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, the term "humanized antibodies" means that at least a portion of the framework regions of an immunoglobulin are derived from human immunoglobulin sequences. A "humanized" antibody includes those such as antibodies with CDR sequences derived from the germline of another species, especially a mammalian species, e.g., a mouse, that have been grafted onto human framework sequences.

In another embodiment, recombinant single chain scFv antibody, preferably a humanized scFv, is used in the methods of the invention.

In one embodiment, the antibodies have the capacity for intracellular transmission. Antibodies which have the capacity for intracellular transmission include antibodies such as camelids and llama antibodies, shark antibodies (IgNARs), scFv antibodies, intrabodies or nanobodies, for example, scFv intrabodies and VHH intrabodies. Such antigen binding agents can be made as described by Harmsen and De Haard, 2007; Tibary et al., 2007; Muyldermans, 2001; and references cited therein.

Anti-CTR antibodies will be known to those skilled in the art and have been used to detect CTR expression in certain tissues. CTR has not been used to date, however, for the detection of cell death. Examples of suitable anti-CTR antibodies include the monoclonal antibody 9B4 disclosed in WO 2009/039584, and MAB4614 (R&D Systems, Inc., USA) which recognizes a discontinuous epitope of CTR.

In certain embodiments, an antibody of the invention has a $V_H$ region consisting of CDR1, CDR2, and CDR3 sequences and a $V_L$ region consisting of CDR1, CDR2, and CDR3 sequences, wherein one or more of these CDR sequences have specified amino acid sequences based on the antibodies described herein or conservative modifications thereof, and wherein the antibodies retain the desired functional property of binding to calcitonin receptor. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

One type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation". Site-directed mutagenesis or PCR-mediated mutagenesis can be performed to introduce the mutation(s) and the effect on antibody binding, or other functional property of interest, can be evaluated in in vitro or in vivo assays. Conservative modifications (as discussed above) can be introduced. The mutations may be amino acid substitutions, additions or deletions. Moreover, typically no more than one, two, or three residues within a CDR region are altered.

Nucleic Acids Encoding Antibodies and Fragments Thereof

Another aspect of the invention relates to nucleic acid molecules that encode the antibodies of the invention or fragments thereof. Examples of full length light chain nucleotide sequences are provided in SEQ ID NOs:47 and 49. Examples of full length heavy chain nucleotide sequences are provided in SEQ ID Nos:46 and 48.

The nucleic acids may be present in whole cells, in a cell lysate, or may be nucleic acids in an isolated, partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

Detectable Labels

As used herein, a "detectable label" is a molecular or atomic tag or marker that generates or can be induced to generate an optical or other signal or product that can be detected visually or by using a suitable detector. Detectable labels are well known in the art and include, without limitation, fluorescent labels, radioisotopes, nanoparticles, chromophores, dyes, enzymes, and contrast agents.

Fluorescent labels commonly used include Alexa, cyanine such as Cy5 and Cy5.5, and indocyanine, and fluorescein isothiocyanate (FITC), but they are not so limited. Fluorescent labels useful in the practice of the invention can include, also without limitation, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); S-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6C; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange+ DNA; Acridine Orange+RNA; Acridine Orange, both DNA & RNA; Acridine Red; Acridine Yellow; Acriflavin; Acriflavin Feulgen SITSA; Aequorin (Photoprotein); Alexa Fluor 350; Alexa Fluor 430; Alexa Fluor 488; Alexa Fluor 532; Alexa Fluor 546; Alexa Fluor 568; Alexa Fluor 594; Alexa Fluor 633; Alexa Fluor 647; Alexa Fluor 660; Alexa Fluor 680; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC=Ratio Dye, $Zn^{2+}$; APTS; Astrazon Brilliant Red 4G; Astrazon Orange R; Astrazon Red 6B; Astrazon Yellow 7 GLL; Atabrine; ATTO-TAG CBQCA; ATTO-TAG FQ; Auramine; Aurophosphine G; Aurophosphine; BAO 9 (Bisamninophenyloxadiazole); BCECF (high pH); BCECF (low pH); Berberine Sulphate; Beta Lactamase; BFP blue shifted GFP (Y66H); Blue Fluorescent Protein; BFP/GFP FRET Bimane; Bisbenzamnide; Bisbenzimide (Hoechst); bis-BTC=Ratio Dye, $Zn^{2+}$; Blancophor FFG; Blancophor SV; BOBO-1; BOBO-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO-1; BO-PRO-3; Brilliant Sulphoflavin FF; BTC-Ratio Dye $Ca^{2+}$; BTC-5Natio Dye, $Zn^{2+}$; Calcein; Calcein Blue; Calcium Crimson; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue; Cascade Yellow 399; Catecholamine; CCF2 (GeneBlazer); CFDA; CFP—Cyan Fluorescent Protein; CFP/YFP; FRET; Chlorophyll; Chromomycin A; Chromomycin A; CL-NERF (Ratio Dye, pH); CMFDA; Coelenterazine; Coelenterazine cp ($Ca^{2+}$ Dye); Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2; Cy3.1 8; Cy3.5; Cy3; Cy5.1 8; Cy5.5; Cy5; Cy7; Cyan GFP; cyclic AMP Fluorosensor (FiCRhR); CyQuant Cell Proliferation Assay; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrohodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrohodamine 123 (DHR); DiI (DiIC18(3)); Dinitrophenol; DiO (DiOC18(3)); DiR; DiR (DiIC18(7)); DM-NERF (high pH); DNP; Dopamine; DsRed; Red fluorescent protein; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyde Induced Fluorescence); FITC; FITC Antibody; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43; FM 4-46; Fura Red (high pH); Fura Red/Fluo-3; Fura-2, high calcium; Fura-2, low calcium; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP), GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; LIVE/DEAD Kit Animal Cells, Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue, LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green; Oregon Green 488; Oregon Green 500; Oregon Greene 514; Pacific Blue; Pararosaniline (Feulgen); PBFI; PE-Cy5; PE-Cy7; PerCP; PerCP-Cy5.5; PE-Texas-Red [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodide (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP; sgBFP (super glow BFP); sgGFP; sgGFP (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYT; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red; Texas Red-X conjugate; Thiadicarbocyanine (DiSC3); Thiazine Red R; Thiazole Orange; Thioflavin 5; Thioflavin 5; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (Tetramethyl-Rodamine-IsoThioCyanate); True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3.

In one embodiment the detectable label is a fluorescent protein. The fluorescent protein can be linked to a compound that binds calcitonin receptor by conventional chemical methods, or it can be expressed together with the compound as a fusion protein. A wide variety of fluorescent proteins are available in a broad range of the light spectrum, including red, orange, yellow-green, green, cyan and UV-excitable green. Non-limiting examples of fluorescent proteins that can be used as labels include mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean, T-Sapphire, Citrine, mYFP, ECFP, mCFP, EBFP, AceGFP (available from Evrogen), AcGFP1 (available from Clontech), AmCyan1 (available from Clontech), AQ143 (available from Lukyanov), AsRed2 (available from Clontech), Azami-Green/mAG (available from MBL Intl.), cOFP (available from Stratagene), CopGFP (available from Evrogen), dimer2, tdimer2(12) (developed by Tsien), DsRed/DsRed2/DsRed-Express (available from Clontech), EBFP (sold by Clontech; no longer commercially available), eqFP611 (developed by Weidenmann), HcRed1 (available from Clontech), HcRed-tandem (available from Evrogen), Kaede (available from MBL Intl.), mBanana (developed by Tsien), mHoneydew (developed by Tsien), MiCy (available from MBL Intl.), mRaspberry (developed by Tsien), mRFP1 (developed by Tsien), mTangerine (developed by Tsien), mYFP (developed by Tsien), PhiYFP (available from Evrogen), Renilla GFPs (various sources), TurboGFP (available from Evrogen) and ZsYellow1 (available from Clontech). In one embodiment the fluorescent label is a far-red fluorescent protein suitable for use in whole-body imaging, such as Katushka and derivatives thereof (Shcherbo et al., 2007).

A detectable label in one embodiment is an enzyme. The enzyme can act on an appropriate substrate to result in production of a detectable dye. Examples of enzymes useful in the invention include, without limitation, alkaline phosphatase and horseradish peroxidase. Alternatively or in addition, the enzyme can be, for example, luciferase. The enzyme can be linked to the compound that binds calcitonin receptor by conventional chemical methods, or it can be expressed together with the compound as a fusion protein.

Radioisotopes useful as detectable labels in the invention are well known in the art and can include $^{3}H$, $^{11}C$, $^{18}F$, $^{35}S$, $^{64}CU$, $^{67}Ga$, $^{68}Ga$, $^{99}mTc$, $^{111}In$, $^{123}I$, $^{124}I$, $^{125}I$ and $^{131}I$. Attachment of any gamma emitting radioactive materials, e.g., $^{99}mTc$ and $^{111}In$, which can react with carboxyl, amino, or sulfhydryl groups of a compound that binds calcitonin receptor is suitable for use in detection methods using gamma scintigraphy. Attachment of radioactive $^{11}C$, $^{18}F$, $^{64}Cu$, $^{67}Ga$, $^{68}Ga$, $^{124}I$, and $^{131}I$ compounds which can react with carboxyl, amino, or sulfhydryl groups of a compound is suitable for use in detection methods using PET/SPECT imaging.

Medical Imaging

Compounds that bind calcitonin receptor can be used in methods of imaging cell death in vivo. In particular, compounds that bind calcitonin receptor and which are conjugated or bound to, and/or coated with, a detectable label, including contrasting agents, can be used in known medical imaging techniques.

For imaging a cell death in vivo, a detectable label may be any molecule or agent that can emit a signal that is detectable by imaging. For example, the detectable label may be a protein, a radioisotope, a fluorophore, a visible light emitting fluorophore, infrared light emitting fluorophore, a metal, a ferromagnetic substance, an electromagnetic emitting substance a substance with a specific MR spectroscopic signature, an X-ray absorbing or reflecting substance, or a sound altering substance.

Examples of imaging methods include MRI, MR spectroscopy, radiography, CT, ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

Certain embodiments of the methods of the present invention further include imaging a tissue during a surgical procedure on a subject. In some embodiments, the subject is undergoing an anticancer therapy such as, but not limited to, chemotherapy, radiation therapy, surgical therapy, immunotherapy, and gene therapy.

A variety of techniques for imaging are known to those of ordinary skill in the art. Any of these techniques can be applied in the context of the imaging methods of the present invention to measure a signal from the detectable label or contrasting agent conjugated to a compound that binds calcitonin receptor. For example, optical imaging is one imaging modality that has gained widespread acceptance in particular areas of medicine. Examples include optical labeling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erytlirosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye.

Gamma camera imaging is contemplated as a method of imaging that can be utilized for measuring a signal derived from the detectable label. One of ordinary skill in the art would be familiar with techniques for application of gamma camera imaging. In one embodiment, measuring a signal can involve use of gamma-camera imaging of an $^{111}$In or $^{99m}$Tc conjugate, in particular $^{111}$In-octreotide or $^{99m}$Tc-somatostatin analogue.

Computerized tomography (CT) is contemplated as an imaging modality in the context of the present invention. By taking a series of X-rays from various angles and then combining them with a computer, CT made it possible to build up a three-dimensional image of any part of the body. A computer is programmed to display two-dimensional slices from any angle and at any depth. The slices may be combined to build three-dimensional representations.

In CT, intravenous injection of a radiopaque contrast agent can assist in the identification and delineation of soft tissue masses when initial CT scans are not diagnostic. Similarly, contrast agents aid in assessing the vascularity of a soft tissue lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol, and iopanoate. Gadolinium agents have also been reported to be of use as a CT contrast agent, for example, gadopentate.

Magnetic resonance imaging (MRI) is an imaging modality that uses a high-strength magnet and radio-frequency signals to produce images. In MRI, the sample to be imaged is placed in a strong static magnetic field and excited with a pulse of radio frequency (RF) radiation to produce a net magnetization in the sample. Various magnetic field gradients and other RF pulses then act to code spatial information into the recorded signals. By collecting and analyzing these signals, it is possible to compute a three-dimensional image which, like a CT image, is normally displayed in two-dimensional slices. The slices may be combined to build three-dimensional representations.

Contrast agents used in MR or MR spectroscopy imaging differ from those used in other imaging techniques. Examples of MRI contrast agents include gadolinium chelates, manganese chelates, chromium chelates, and iron particles. Both CT and MRI provide anatomical information that aid in distinguishing tissue boundaries and vascular structure.

Imaging modalities that provide information pertaining to information at the cellular level, such as cellular viability, include positron emission tomography (PET) and single-photon emission computed tomography (SPECT). In PET, a patient ingests or is injected with a radioactive substance that emits positrons, which can be monitored as the substance moves through the body.

Closely related to PET is single-photon emission computed tomography, or SPECT. The major difference between the two is that instead of a positron-emitting substance, SPECT uses a radioactive tracer that emits high-energy photons. SPECT is valuable for diagnosing multiple illnesses including coronary artery disease, and already some 2.5 million SPECT heart studies are done in the United States each year. PET radiopharmaceuticals for imaging are commonly labelled with positron-emitters such as $^{11}$C, $^{13}$N, $^{15}$O, $^{18}$F, $^{82}$Rb, $^{62}$Cu, and $^{68}$Ga. SPECT radiopharmaceuticals are commonly labelled with positron emitters such as 99mTc, $^{201}$Tl, and $^{67}$Ga, $^{111}$In.

Diagnosis, Prognosis, and/or Prediction of Therapeutic Outcome

In one embodiment, the present invention provides a method of diagnosis, prognosis and/or prediction of therapeutic outcome in a subject, the method comprising performing the method of the invention on a subject, on a sample comprising cells obtained from a subject, or on cells obtained from the subject in order to detect cell death.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease.

As used herein, the phrase "prediction of therapeutic outcome" and the terms "predicting", "predictive" and variants thereof refer to determining the probability of response to a therapeutic agent or modality, for example, determining the probability of the sensitivity of a cancer cell to a chemotherapeutic agent or a radiotherapeutic agent, or determining the probability of survival or recurrence of disease.

The subject may have or be suspected of having a condition associated with cell death. As used herein, a "condition associated with cell death" is a condition such as a disease or disorder which has cell death, such as for example, apoptosis, anoikis, autophagy or necrosis, as a feature characteristic of that condition. An important condition associated with cell death is cancer. Additional conditions associated with cell death include, without limitation, chemotherapy-, radiation-, or hormone-induced cell death in solid and hematological tumors; tumor resistance to therapy; acute cardiac allograft rejection; acute myocardial infarction; anthracycline-induced cardiotoxicity; arrhythmogenic right ventricle dysplasia; skeletal muscle apoptosis; congestive heart failure; coronary artery disease; atherosclerosis; infectious endocarditis; myocarditis; myocardial dysfunction; myocardial ischemia-reperfusion injury; non-cardiac allograft rejection; graft-versus-host disease; bacterial infection; viral infection; multiple organ dysfunction syndrome; septic shock; cerebral ischemia-reperfusion injury; macular degeneration; neurodegenerative disease; central nervous system trauma; autoimmune diabetes mellitus; rheumatoid arthritis; systemic lupus erythematosus; inflammatory bowel disease; multiple sclerosis; other autoimmune diseases; annexinopathies; osteoarthritis; renal failure; chronic renal atrophy and renal fibrosis; glomerular injury; and polycystic renal disease.

The diagnostic, prognostic and predictive methods of the present invention may involve a degree of quantification to determine levels of the compound that binds calcitonin receptor in patient samples. Such quantification is readily provided by the inclusion of appropriate reference samples.

In one embodiment the method involves monitoring cell death in the subject using the method of the invention described herein. In various embodiments the monitoring can be performed in vitro on cells or a sample obtained from the subject or in vivo. Monitoring generally involves comparing cell death in the subject, or in cells or a sample from the subject, as measured on at least two occasions, for example, before and after treatment. The monitoring thus can be performed to judge the effectiveness of a treatment and/or the status of a condition being treated. For example, the method of the invention is useful for evaluating the effectiveness of an anti-cancer treatment, such as an immunotherapy, a chemotherapy and a radiation therapy.

Screening Assays

The present invention provides a method of screening (i.e. a screening assay) for a modulator, such as an inducer or inhibitor, of cell death. In one embodiment the modulator identified by the method is an inhibitor of cell death, for example, an anti-apoptotic agent. In another embodiment the modulator identified by the method is a stimulator or inducer of cell death. The screening assay can be performed in vitro or in vivo.

In one embodiment, a screening assay is a cell-based assay in which a cell which is undergoing cell death, or is subjected to cell death-inducing conditions, is contacted with a test compound and the ability of the test compound to inhibit cell death determined. The cell, for example, can be a cell of mammalian, avian, fish or invertebrate origin. In one embodiment the cell is a human cell or a mouse cell. Determining the ability of the test compound to inhibit cell death can be accomplished, for example, by using a conjugate labelled with a fluorescent, radioisotopic, or enzymatic label such that uptake of the label can be determined by detecting the labelled conjugate in the cell. For example, conjugates can be labelled with $^{125}I$, $^{35}S$, $^{14}C$, or $^{3}H$, either directly or indirectly, and the radioisotope detected by direct counting of radio-emission or by scintillation counting. Alternatively, conjugates can be enzymatically labelled with, for example, horseradish peroxidase, alkaline phosphatase, or luciferase, and the enzymatic label detected by determination of conversion of an appropriate substrate to product.

Inhibitors of cell death are known in the art. By way of non-limiting example, known inhibitors of apoptosis include cyclocreatine, cyclocreatine phosphate, coenzyme Q10, L-carnitine, glutathione, α-lipoic acid, BCL-2 family members, for example BCL-2 and BCL-$X_L$, and peptide derivatives thereof, as well as for example Caspase Inhibitors I to IV, VI, VIII and X, Caspase 2 Inhibitors, Caspase 3 Inhibitors as well as other caspase inhibitors known in the art Inhibitors of autophagy are known in the art and include chloroquine and its analogue hydroxychloroquine, and lucanthone.

In one embodiment, the screening assay comprises contacting the cell with a compound which is known to induce cell death, contacting the cell with a test compound, and determining the ability of the test compound to inhibit cell death, wherein determining the ability of the test compound to inhibit cell death comprises determining the uptake of conjugate by the cell, or labelling of the cell, in the presence of the test compound compared to the uptake of conjugate by the cell, or labelling of the cell, in the presence of the known compound alone. A reduced level of uptake of the conjugate by the cell or labelling of the cell in the presence of the test compound indicates the test compound is an inhibitor of cell death.

As known in the art, cell-death inducing conditions include gamma radiation, UV radiation and cell-death inducing agents include a variety of chemotherapeutic drugs, including cisplatin, doxorubicin, bleomycin, cytosine arabinoside, nitrogen mustard, methotrexate and vincristine, as well as ethanol and d-amyloid peptide.

Inducers of autophagy include, but are not limited to histone deacetylase (HDAC) inhibitors, tamoxifen, EB1089, anti-angiogenic agents, tyrosine kinase inhibitors, resveratrol, alkylating agents, arsenic trioxide, Akt inhibitors, HIV protease inhibitors, and mammalian target of rapamycin (mTOR) inhibitors. Inhibitors of autophagy include, but are not limited to chloroquine, hydroxychloroquine, omeprazole, BMS1, BMS2, BMS3, and BMS4, and microtubule disrupting agents For example, see Bialik and Kimchi (2008).

In one embodiment, the screening assay is a cell-based assay comprising contacting a cell that is not undergoing cell death or is not subjected to cell death-inducing conditions with a test compound and determining the ability of the test compound to stimulate or induce cell death. Determining the ability of the test compound to stimulate or induce cell death can be accomplished, for example, by determining the uptake of conjugate by the cell in the presence of the test compound compared to the uptake of conjugate by the cell in the absence of the test compound. An increased level of uptake of the conjugate by the cell in the presence of the test compound indicates the test compound is a stimulator or inducer of cell death.

In vitro screening methods of the invention can be adapted and performed as high-throughput screening assays. General methods for high-throughput screening assays are well known in the art and can include the use of samples presented in arrays, for example in multi-well plate format, that can be processed either manually or, conveniently, with automated or semi-automated sample and/or fluid handling devices adapted for use with a particular array format. For example, in one embodiment data are obtained using a 96-well format flow cytometer. In one embodiment high-throughput screening methods employ a high information content screening platform such as is commercially available from Cellomics (Thermo Fisher Scientific, Waltham, Mass.). The platforms in essence take a photomicrograph of each well of a 96- or 384-well multi-plate, and then use image analysis to score for desired phenotypes (e.g., fluorescence). In this case, a fluorescent probe (or other suitable probe) can be added directly to the medium and directly scored since the dead cells will take up and concentrate the probe, which can be distinguished from the background fluorescence in the medium. High-throughput screening methods generally permit screening of dozens, hundreds, even thousands of samples in a day.

Screening Candidate Pesticides/Insecticides

One of the major difficulties facing the agricultural and horticultural industries is the control of insect and other pathogen infestation of plants or animals. Insects and other pathogens account for millions of tonnes of lost production on an annual basis. Plants are vulnerable to pests such as insects during germination, sprouting and growth, particularly initial growth because the growing plant is small and even a small amount of pest-mediated damage can cause the loss of the entire plant. Moreover, some natural plant defences are not fully developed at these stages of plant development, rendering the plant even more vulnerable to pests. In one embodiment, the invention provides assays for detecting cell death in a plant pest or animal pest, or in cells of the plant pest or animal pest. Thus, the assay of the invention may be used for the purpose of testing candidate pesticide or insecticide compounds for the ability to cause cell death in a plant pest or animal pest. In one embodiment, the plant or animal pest is an insect.

Plant pests include, but are not limited to, pest nematodes (e.g., cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., and foliar nematodes *Aphelenchus* spp. or *Aphelenchoides* spp.), pest molluscs (slugs and snails), and insects (e.g., corn rootworms, *Lygus* spp., aphids, corn borers, cutworms, armyworms, leafhoppers, Japanese beetles, grasshoppers, and other pest coleopterans, dipterans, and lepidopterans).

In one embodiment, the animal or plant pest is selected from *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus*, *Reticulitermes flavipes*, *R. speratu*, *R. virginicus*, *R. hesperus*, and *R. santonensis*) and the Termitidae (for example *Globitermes sulfureus*), *Solenopsis geminata* (fire ant), *Monomorium pharaonic* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

By way of example, a plant or animal pest, or cells from the pest may be contacted with one or more candidate pesticides or insecticides. The pest or pest cells are then contacted with a compound which binds to calcitonin receptor in order to detect the level of calcitonin receptor in the pest or pest cells treated with the candidate pesticide or insecticide. The level of binding of the anti-CTR compound in the pest or pest cells can be compared with suitable control or reference samples, for example pest or pest cells that have not been treated with the candidate pesticide or insecticide. An increased level of binding of the anti-CTR compound in the pest or pest cells compared to the reference or control samples is indicative that the candidate pesticide or insecticide is causing cell death in the pest. Thus, the assay of the invention can be used to evaluate candidate pesticide and insecticide compositions.

Reference Samples

In some embodiments, the skilled person will compare the detected level of the compound that binds calcitonin receptor with a reference sample. For example, the method may comprise measuring the level of the compound in or on a cell or in or on a population of cells and comparing the level of the compound to a reference level of the compound in or on a reference sample or reference population of cells.

In one embodiment, the reference sample or reference population of cells comprises cells not undergoing cell death, and the method comprises determining (a) there is a higher amount of cell death when the level of the compound is greater than the reference level, or (b) there is a lower amount of cell death when the level of the compound is less than the reference level.

In another embodiment, the reference sample or reference population of cells comprises cells undergoing cell death or cells treated to induce cell death.

As will be known to those skilled in the art, when internal reference samples or reference populations of cells are not included in each assay conducted, the reference may be an established data set.

Established data sets may be selected from, for example:

1. a data set comprising measurements of the level of a compound that binds calcitonin receptor in a cell or population of cells in vitro, wherein the cell or population of cells are undergoing cell death or have been treated to induce cell death.

2. a data set comprising measurements of the level of a compound that binds calcitonin receptor in a cell or population of cells in vitro, wherein the cell or population of cells is not undergoing cell death or has been treated with an inhibitor of cell death.

3. a data set comprising measurements of the level of a compound that binds calcitonin receptor in a cell or population of cells from subjects known to have a condition associated with cell death;

4. a data set comprising measurements of the level of a compound that binds calcitonin receptor in a cell or population of cells from a subject being tested wherein said measurements have been made previously, such as, for example, when the subject was known to be healthy or, in the case of a subject having a condition associated with cell death, when the subject was diagnosed or at an earlier stage in disease progression;

5. a data set comprising measurements of the level of a compound that binds calcitonin receptor in a cell or population of cells for a healthy individual or a population of healthy individuals; and 6. a data set comprising measurements of the level of a compound that binds calcitonin receptor in a cell or population of cells for a normal individual or a population of normal individuals.

In the present context, the term "typical population" with respect to subjects known to have a condition associated with cell death shall be taken to refer to a population or sample of subjects diagnosed with a condition that is associated with cell death that is representative of the spectrum of the patients suffering the condition. This is not to be taken as requiring a strict normal distribution of morphological or clinicopathological parameters in the population, since some variation in such a distribution is permissible. Preferably, a "typical population" will exhibit a spectrum of the condition at different stages of disease progression.

As will be known to those skilled in the art, data obtained from a sufficiently large sample of the population will normalize, allowing the generation of a data set for determining the average level of compound that binds calcitonin receptor in a cell or population of cells. Those skilled in the art are readily capable of determining the baseline for comparison in any diagnostic assay of the present invention without undue experimentation, based upon the teaching provided herein.

EXAMPLES

Example 1

Antibodies

These studies involved the use of two mouse monoclonal anti-human CTR antibodies, one directed against an extracellular epitope (MAb 46/08-2C4, IgG1, Welcome Receptor Antibodies Pty Ltd [WRA, www.WelcomeReceptor.com], Melbourne), and the second against a cytoplasmic epitope (Wookey et al., 2008; Wookey et al., 2012; MAb 31/01-1H10, IgG2A, WRA, Melbourne; distributed as MCA 2191 by AbD Serotec, UK).

Previous studies using MCA 2191 have been published (Wookey et al., 2008; Wookey et al., 2009; Silvestris et al., 2008; Wookey et al. 2012) which have demonstrated the high quality of this antibody in immunohistochemical experiments. Furthermore fluorescence activated cell sorting (FACS) analysis of CTR-positive cells as well as stable transfectants of COS-7 cell lines that are positive and negative for CTR (unpublished data) has been demonstrated.

For the confocal analysis and multi-labeling immunofluorescence experiments the antibodies used included the anti-CTR antibodies (above), the anti-cleaved caspase 3 antibody (#9579, Cell Signaling, Beverly, Mass., USA) with goat anti-rabbit:AF635 (Life Technologies, Carlsbad, Calif., USA), and the annexin V detection kit (TACS Annexin V-biotin, Trevingen, Gaithersburg, Md., USA) with streptavidin:AF488 (Life Technologies). The isotype control antibody MAb 9E10 (anti-myc, IgG1; Evan et al., 1985) conjugated with the Alexafluor 647 using the same technique for MAb 2C4 described below.

Both anti-CTR monoclonal antibody MAb 2C4 and anti-cMyc monoclonal MAb 9E10 (isotype control) were conjugated to AlexaFlour succinamide esters (LifeTechnologies) using standard techniques. In brief, antibodies were buffer exchanged into 100 mM $NaHCO_3$, pH 8.3, and concentrated to 10 mg/mL using 10 kDa MWCO centrifugal filter (Millipore). 5 mg of antibody was reacted with 5 µg of Alexa Flour succinmide ester (either AF568 or AF647) in the dark at room temperature for 1 hour. Unreacted succinamide ester was removed by multiple buffer exchanges into PBS using a 10 kDa MWCO centrifugal filter. A small amount of purified, conjugated antibody was subjected to analytical size exclusion chromatography using a Superdex S200 column (GE Healthcare, Piscaway, N.J., USA) on a Biologic Dual flow FPLC (BioRad, Hercules Calif., USA) to confirm the absence of unreacted succinamide ester. The degree of labelling was determined according to the manufacturers recommendations (LifeTechnologies) on a Nanodrop1000 spectrophotometer (Thermo Scientific, Cambridge, UK).

Example 2

Cell Culture

The human sarcoma cell line MG63 was cultured in MEMα (Life Technologies) plus 10% foetal bovine serum (FBS, Life Technologies). The human glioblastoma cell line A172 and monkey kidney cell line COS-7 were cultured in Dulbecco's modified Eagle's medium (DMEM, Life Technologies) plus 10% FBS. The high grade glioma cell line GBM-L2 was cultured in StemPro media (serum free, Life Technologies A10509-01). Cultured cells were incubated in a humidified 37° C. incubator with 5% $CO_2$.

Four-well slides (Nunc 154526, Lab Tek II chamber slides for cell lines A172 and COS-7 and Nunc 154917, CC2 coated for GBM-L2 cells, ThermoFisher Scientific, Rochester, N.Y., USA) were seeded with 50,000 cells/mL of media/chamber and grown in a humidified 37° C. incubator with 5% $CO_2$ until 50-80% confluence. A range of concentrations of the cytotoxin staurosporine (final $10^{-6}$, $10^{-7}$ and $10^{-8}$ M, Sigma Aldrich, St Louis, Mo., USA) were introduced for 19 hours to induce apoptosis. The cells were washed once in media and 10 µg/mL of MAb 2C4:AF568 introduced with further incubation for 30 minutes (live cell staining step). The chambers were washed in cold binding buffer and annexin V:biotin (Trevigen Inc.) added for 15 minutes. The chambers were then washed and fixed in 4% paraformaldehyde [ProSci Tech, Australia]/PBS (pH 7.2) for 30 minutes. After washing in once in PBS and twice in PBS/1% Triton-X100 [Sigma Aldrich] and blocking (1% BSA [Roche, Mannheim, Germany], 5% NGS in PBS/1% Triton-X100) for 1 hour at room temperature, the primary anti-caspase 3 antibody (1:200) was introduced overnight at 6° C. in a humidified chamber. The following day the chambers were washed three times in PBS and the cells incubated in the dark at room temperature for 60 minutes with the secondary antibody (goat anti-rabbit:AF635 [Life Technologies], 1:500 in PBS) and streptavidin:AF488 (Life Technologies). The slides were washed three times and the chambers were removed prior to mounting with DAPI aqueous mount (Prolong Gold, Life Technologies) and dried at room temperature for several days in the dark.

Example 3

Confocal Microscopy of Cell Lines and Immunofluorescence

The samples were imaged by confocal microscopy (Objectives ×20, ×40, ×63) on a Zeiss Imager Z1/LSM 510 Meta confocal laser scanning system (Zeiss, Oberkocken, Germany) using Zen software (Zeiss). DAPI (405 nm, ProLong Gold) was used to visualise the nuclei. Images (LSM format, Zeiss) were captured in a single focal plane (optical sections of 0.7 μm nominal thickness).

Example 4

InCell Analysis

Quantitative analysis of apoptosis of MG63 cells was performed using an InCell Analyzer 2000 (GE Healthcare, USA) high content imaging platform. Cells were cultured overnight under standard conditions in 96-well ViewPates (Perkin Elmer, Waltham, Mass., USA). On the day of assay the media was removed, cells washed with phenol red-free DMEM (#21063, LifeTechnologies) then incubated in phenol red-free DMEM in the presence of 10 μM Hoechst 33342 (LifeTechnologies) for 1 hour prior to initiating the assay with the addition of 1 μM staurosporine (LifeTechnologies) and MAb 2C4:AF568 antibodies at 30 ng/mL. Images were acquired with four fields of view per well using a 20× objective. Experiments were performed in duplicate wells. Image analysis and quantification of was performed using InCell Analyzer Work station 3.5 software (InCell Investigator, GE Healthcare). The UV channel (Hoechst 33342) was used to define and count nuclei, the bright-field to define whole cell area, the red channel to quantify number of MAb2C4:AF568-positive events using granularity analysis, and far red for the isotype (MAb9E10:AF647) control. These fluorophores were used for calculation of numbers of MAb2C4:AF568-positive events normalised to total cell numbers. A further control with MAb2C4:AF568 but in the absence of induced apoptosis was determined.

Example 5

Detection of Apoptotic and Necrotic Cells with Anti-CTR Antibody:Fluorophore Conjugate MAb2C4 is a mouse anti-human CTR antibody (IgG1) that binds an extracellular epitope and has been conjugated with AlexaFluor 568 (MAb2C4:AF568). It binds apoptotic cells and is accumulated into dead cells to produce a high fluorescence event. MAb2C4:AF568 was validated using cell lines expressing human calcitonin receptor (hCTR).

MAbFLAG:AF568 is an IgG1 isotype control. This conjugate was validated using a stable transfectant HEK293 cell line that expresses the PA receptor tagged with a FLAG epitope sequence. The FLAG epitope is positioned on the cell surface. Annexin V:AF488 binds the plasma membrane of dying (apoptotic) and dead (necrotic) cells.

The results of cell staining with anti-CTR antibodies are shown in FIGS. 5 to 10. These results demonstrate that an antibody against a specific primary epitope of human CTR conjugated to a fluorophore is useful for the determination of the extent of cell populations undergoing Programmed Cell Death including apoptotic, transitional and necrotic (dead) subpopulations, as determined by fluorescence activated cell sorting (FACS).

Example 6

Cloning and Sequencing of Antibody $V_H$ and VL Gene Fragments Using Four Hybridoma Cell Lines The cloning and sequencing of antibody VH and VL gene fragments was performed by CSIRO Consultancy and Technical Services on a fee-for service basis. Altogether eight (8) antibody variable cDNA gene fragments (4×VH & 4×VL) were extracted and PCR-amplified from four different hybridoma cell lysates: 1) 2C4 (IgG1/kappa), 2) 6G11 (IgG2a/kappa), 3) 9B4 (IgG2a/kappa), 4) 10D1 (IgG2a/kappa). Extracted gene fragments were subsequently cloned into StrataClone cloning vector and their DNA sequences determined using Micromon sequencing facility (Monash University). The following pages in this report describe 1) the methodology used for cloning of these cDNA genes, and 2) final DNA and predicted protein sequences of these V gene fragments.

Reagents

Hybridoma cells supplied as cell homogenates in TRIZOL reagent (1 ml).

Oligotex mRNA Mini Kit (Qiagen, Cat. #70022; Lot No 145047688)

Omniscript® Reverse Transcriptase kit (Qiagen, Cat. #205111, Lot 145044884)

MN Clean-up Kit (Ref. 740609.250)

Terminal Transferase TdT (Finnzymes, Cat # F203, Lot #00115553)

Phusion Polymerase (New England Biolabs; F530S Lot 00157424)

StrataClone PCR Cloning Kit (Cat#240205).

Bioline Isolate II Plasmid Miniprep Kit (BIO-52056 IS493-213D)

Design of Oligonucleotide Primers

Oligonucleotide primers utilised in the course of this work were designed according to Kabat antibody sequence database (Kabat et al., 1991) and synthesised at Geneworks Pty Ltd (South Australia).

Extraction and Purification of Poly-A+RNA

Total cellular RNA was extracted from $5 \times 10^6$ hybridoma cell lines using TRIZOL reagent and the procedure recommended by the reagent's manufacturer. Poly-A+RNA was isolated from total RNA using Oligotex mRNA mini kit.

$V_H$ and $V_L$ cDNA Synthesis and Purification

Poly-A+ RNA was reverse transcribed using Omniscript® Reverse Transcriptase kit and anti-sense oligonucleotides that annealed to mouse light or heavy chain constant region sequence approximately 100 bases downstream of J and C exons junction. Approximately 200 ng of poly-A+ and 10 pmol of isotype-specific primer was used to generate 1st strand cDNA. Oligonucleotide primers that did not match the predicted isotype of light and heavy chain cDNA being transcribed were included in these RT reactions for negative control purposes. RT reactions were incubated at 37° C. for 1 hour and the resulting $1^{st}$ cDNA was purified using MN clean-up kit according to instructions supplied by the manufacturer.

Single strand cDNA was eluted from an MN Clean-up column with 40 μl of water. Terminal transferase was used to add poly-G tail at the 3'-end by incubating the reaction mixture, at 37° C. for 30 min. Poly-G tailed ss-cDNA was again purified MN clean-up kit and eluted with 40 µl of elution buffer. The G-tailed cDNA was amplified by PCR using Vent polymerase. The poly-C anchor sense primer and anti-sense CH or CL specific primers that annealed to the antibody DNA sequence located at the start of CH and CL constant region (approximately 40 bases downstream of J-C exons junction). PCR's were carried out with up to 30 cycles of 30 sec denaturation at 98° C., 15 sec annealing at 55° C. and 15 sec extension at 72° C. Amplified DNA fragments were analysed on 1% (w/v) agarose gel and major bands of ~550 bp for VL and 600 bp for VH were excised from the gel using MN Clean up kit. Resulting cDNA fragments were eluted from the MN column with 30 µl of water and its concentration and purity estimated using UV spectroscopy, assuming A260=1 for 50 µg/ml DNA solution.

Cloning of $V_H$ and $V_L$ for DNA Sequencing Analysis

Amplified DNA fragments were ligated into a sequencing vector using the StrataClone Blunt PCR Cloning kit and instructions specified therein. StrataClone E. coli competent cells were transformed with 2 µl of ligation mix according to the method within the StrataClone kit. Transformed colonies (≥8) were screened using colony PCR with USP and RSP primers for the presence of DNA fragment insert of ≥700 bp.

Sequencing and Sequencing Analysis of $V_H$ and $V_L$ cDNA Clones

Putative positive colonies were picked and miniprep DNA was prepared using Bioline Isolate Plasmid Miniprep kit. Sequencing reactions were performed and resolved using Micromon DNA sequencing facility (Monash University). Sequence data obtained were analysed using Vector NTI Advance software version 11.5.2 (Life Technologies).

DNA and Protein Sequence Alignments and Analysis

Analysis of sequencing data indicated that all four hybridoma cell lines generated good quality $V_H$ and $V_L$ cDNA sequences. Final sequence identification was easy as four or more identical $V_H$ and $V_L$ cDNA sequences were obtained for each cell line. $V_H$ and $V_L$ cDNA sequences were extracted using oligonucleotide primers located within constant region of light and heavy chains. Consequently all cDNA sequences included: 1) leader peptide sequence, 2) $V_H$ or $V_L$ sequence, and 3) part of CH1 or CL sequence.

The protein sequences for all eight cDNA fragments (4× heavy chain and 4× light chain) cloned and analysed in this project are provided as SEQ ID Nos:46 to 51. CDR residues were determined according to 1) structural loop definition of Chothia and primary sequence definition of Kabat (residues in bold). The rational behind definitions of CDR residues can be found at http://www.bionf.org.uk/abs/#cdrid.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

All publications discussed and/or referenced herein are incorporated herein in their entirety.

The present application claims priority from AU 2013904574, the entire contents of which are incorporated herein by reference.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

REFERENCES

Bialik and Kimchi (2008) Adv Exp Med Biol, 615:177-200.
Bird et al. (1988) Science, 242:423-426.
Boros et al. (2005) J Org Chem, 70:5331-5334.
Evan et al. (1985) Mol Cell Biol, 5:3610-3616.
Huston et al. (1988) Proc Natl Acad Sci USA, 85:5879-5883.
Goldring et al. (1993) Horm Metab Res, 25:477-480.
Gorn et al. (1995) J Clin Invest, 95:2680-2691.
Harmsen and De Haard (2007) Appl Microbiol Biotechnol, 77:13-22.
Hirsch and Baruch (2003) Endocrine. 21:201-208.
Jones et al. (1986) Nature, 321:522-525.
Lin et al. (1991) Science. 254:1022-1024.
Masi et al. (1998) Biochem Biophys Res Commun, 245: 622-626.
Morrison et al. (1984) Proc Natl Acad Sci USA, 81:6851-6855.
Muyldermans (2001) J Biotechnol, 74:277-302.
Nakamura et al. (1997) Hum Genet, 99:38-41.
Shcherbo et al. (2007) Nat Methods, 4:761-766.
Silvestris et al. (2008) Leuk Res, 32:611-623.
Tibary et al. (2007) Soc Reprod Fertil Suppl, 64:297-313.
Wookey et al. (2008) Histopathol, 52:605-612.
Wookey et al. (2009) Histochem Cell Biol, 132:181-189.
Wookey et al. (2012) Histopathol, 60:895-910.

The invention claimed is:

1. A method for detecting cell death in a cell, the method comprising:
   i) contacting a cell with a compound that binds calcitonin receptor, and
   ii) detecting the compound in or on the cell,
   wherein the level of the compound in or on the cell is indicative of cell death, and wherein the compound that binds calcitonin receptor is an antibody conjugated to a detectable label, wherein the antibody binds an epitope within an amino acid sequence provided as any one of SEQ ID NOs:6 to 12.

2. The method of claim 1, wherein the method further comprises comparing the level of the compound in or on the cell with the level of the compound in or on a cell in a reference sample.

3. The method of claim 1, wherein the method comprises measuring the level of the compound in or on a population of cells and comparing the level of the compound to a reference level of the compound in or on a reference population of cells.

4. The method of claim 2, wherein the reference sample comprises cells not undergoing cell death, and wherein the method comprises determining (a) if there is a higher amount of cell death when the level of the compound is greater than the reference level, or (b) if there is a lower amount of cell death when the level of the compound is less than the reference level.

5. The method of claim 2, wherein the reference sample comprises cells undergoing cell death or cells treated to induce cell death.

6. The method of claim 1, wherein the detectable label is selected from a radiolabel, an enzyme, a fluorescent label, a luminescent label, a bioluminescent label, a magnetic label and/or biotin.

7. The method of claim 1 which is performed on a cell or population of cells in vitro.

8. The method of claim 7, wherein the method is performed on cells obtained from a subject.

9. The method of claim 1, wherein the method comprises administering to a subject a compound that binds calcitonin receptor and determining the level of the compound in or on cells in a sample obtained from the subject, wherein the level of the compound is indicative of the level of cell death.

10. The method of claim 1, wherein the method of detecting cell death in a cell comprises a method of imaging cells undergoing cell death.

11. The method of claim 3, wherein the reference population of cells comprises cells undergoing cell death or cells treated to induce cell death.

* * * * *

SEQUENCE LISTING

```
<160> NUMBER OF SEQ ID NOS: 54

<210> SEQ ID NO 1
<211> LENGTH: 490
<212> TYPE: PRT
<213> ORGANISM: Homo sapiens

<400> SEQUENCE: 1

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45
```

```
Met Asp Ala Gln Tyr Lys Cys Tyr Asp Arg Met Gln Gln Leu Pro Ala
    50              55                  60
Tyr Gln Gly Glu Gly Pro Tyr Cys Asn Arg Thr Trp Asp Gly Trp Leu
65              70                  75                  80
Cys Trp Asp Asp Thr Pro Ala Gly Val Leu Ser Tyr Gln Phe Cys Pro
                85              90                  95
Asp Tyr Phe Pro Asp Phe Asp Pro Ser Glu Lys Val Thr Lys Tyr Cys
                100             105                 110
Asp Glu Lys Gly Val Trp Phe Lys His Pro Glu Asn Asn Arg Thr Trp
            115             120                 125
Ser Asn Tyr Thr Met Cys Asn Ala Phe Thr Pro Glu Lys Leu Lys Asn
    130             135                 140
Ala Tyr Val Leu Tyr Leu Ala Ile Val Gly His Ser Leu Ser Ile
145             150                 155                 160
Phe Thr Leu Val Ile Ser Leu Gly Ile Phe Val Phe Arg Lys Leu
                165             170                 175
Thr Thr Ile Phe Pro Leu Asn Trp Lys Tyr Arg Lys Ala Leu Ser Leu
                180             185                 190
Gly Cys Gln Arg Val Thr Leu His Lys Asn Met Phe Leu Thr Tyr Ile
    195             200                 205
Leu Asn Ser Met Ile Ile Ile His Leu Val Glu Val Val Pro Asn
    210             215                 220
Gly Glu Leu Val Arg Arg Asp Pro Val Ser Cys Lys Ile Leu His Phe
225             230                 235                 240
Phe His Gln Tyr Met Met Ala Cys Asn Tyr Phe Trp Met Leu Cys Glu
                245             250                 255
Gly Ile Tyr Leu His Thr Leu Ile Val Val Ala Val Phe Thr Glu Lys
                260             265                 270
Gln Arg Leu Arg Trp Tyr Tyr Leu Leu Gly Trp Gly Phe Pro Leu Val
            275             280                 285
Pro Thr Thr Ile His Ala Ile Thr Arg Ala Val Tyr Phe Asn Asp Asn
    290             295                 300
Cys Trp Leu Ser Val Glu Thr His Leu Leu Tyr Ile Ile His Gly Pro
305             310                 315                 320
Val Met Ala Ala Leu Val Val Asn Phe Phe Phe Leu Leu Asn Ile Val
                325             330                 335
Arg Val Leu Val Thr Lys Met Arg Glu Thr His Glu Ala Glu Ser His
                340             345                 350
Met Tyr Leu Lys Ala Val Lys Ala Thr Met Ile Leu Val Pro Leu Leu
            355             360                 365
Gly Ile Gln Phe Val Val Phe Pro Trp Arg Pro Ser Asn Lys Met Leu
370             375                 380
Gly Lys Ile Tyr Asp Tyr Val Met His Ser Leu Ile His Phe Gln Gly
385             390                 395                 400
Phe Phe Val Ala Thr Ile Tyr Cys Phe Cys Asn Asn Glu Val Gln Thr
                405                 410                 415
Thr Val Lys Arg Gln Trp Ala Gln Phe Lys Ile Gln Trp Asn Gln Arg
            420             425                 430
Trp Gly Arg Arg Pro Ser Asn Arg Ser Ala Arg Ala Ala Ala Ala
            435             440                 445
Ala Glu Ala Gly Asp Ile Pro Ile Tyr Ile Cys His Gln Glu Pro Arg
    450             455                 460
Asn Glu Pro Ala Asn Asn Gln Gly Glu Glu Ser Ala Glu Ile Ile Pro
```

Leu Asn Ile Ile Glu Gln Glu Ser Ser Ala
465                 470                 475                 480

485                 490

<210> SEQ ID NO 2
<211> LENGTH: 516
<212> TYPE: PRT
<213> ORGANISM: Mus musculus

<400> SEQUENCE: 2

Met Arg Phe Leu Leu Val Asn Arg Phe Thr Leu Leu Leu Leu Leu
1               5                   10                  15

Val Ser Pro Thr Pro Val Leu Gln Ala Pro Thr Asn Leu Thr Asp Ser
                20                  25                  30

Gly Leu Asp Gln Glu Pro Phe Leu Tyr Leu Val Gly Arg Lys Lys Leu
            35                  40                  45

Leu Asp Ala Gln Tyr Lys Cys Tyr Asp Arg Ile His Gln Leu Pro Ser
50                  55                  60

Tyr Glu Gly Glu Gly Leu Tyr Cys Asn Arg Thr Trp Asp Gly Trp Met
65                      70                  75                  80

Cys Trp Asp Asp Thr Pro Ala Gly Ala Thr Ala Tyr Gln His Cys Pro
                85                  90                  95

Asp Tyr Phe Pro Asp Phe Asp Thr Ala Glu Lys Val Ser Lys Tyr Cys
                100                 105                 110

Asp Glu Asn Gly Glu Trp Phe Arg His Pro Asp Ser Asn Arg Thr Trp
            115                 120                 125

Ser Asn Tyr Thr Leu Cys Asn Ala Phe Thr Ser Glu Lys Leu Gln Asn
            130                 135                 140

Ala Tyr Val Leu Tyr Tyr Leu Ala Leu Val Gly His Ser Leu Ser Ile
145                 150                 155                 160

Ala Ala Leu Val Ala Ser Met Leu Ile Phe Trp Ile Phe Lys Asn Leu
                165                 170                 175

Ser Cys Gln Arg Val Thr Leu His Lys His Met Phe Leu Thr Tyr Ile
            180                 185                 190

Leu Asn Ser Ile Ile Ile Ile Ile His Leu Val Glu Val Val Pro Asn
            195                 200                 205

Gly Asp Leu Val Arg Arg Asp Pro Met His Ile Phe His His Asn Thr
210                 215                 220

His Met Trp Thr Met Gln Trp Glu Leu Ser Pro Pro Leu Pro Leu Ser
225                 230                 235                 240

Ala His Glu Gly Lys Met Asp Pro His Ala Ser Glu Val Ile Ser Cys
                245                 250                 255

Lys Val Leu His Phe Leu His Gln Tyr Met Met Ser Cys Asn Tyr Phe
            260                 265                 270

Trp Met Leu Cys Glu Gly Ile Tyr Leu His Thr Leu Ile Val Met Ala
            275                 280                 285

Val Phe Thr Asp Glu Gln Arg Leu Arg Trp Tyr Tyr Leu Leu Gly Trp
            290                 295                 300

Gly Phe Pro Ile Val Pro Thr Ile Ile His Ala Ile Thr Arg Ala Leu
305                 310                 315                 320

Tyr Tyr Asn Asp Asn Cys Trp Leu Ser Ala Glu Thr His Leu Leu Tyr
                325                 330                 335

Ile Ile His Gly Pro Val Met Val Ala Leu Val Val Asn Phe Phe
            340                 345                 350

-continued

```
Leu Leu Asn Ile Val Arg Val Leu Val Thr Lys Met Arg Gln Thr His
            355                 360                 365
Glu Ala Glu Ser Tyr Met Tyr Leu Lys Ala Val Lys Ala Thr Met Val
    370                 375                 380
Leu Val Pro Leu Leu Gly Ile Gln Phe Val Val Phe Pro Trp Arg Pro
385                 390                 395                 400
Ser Asn Lys Val Leu Gly Lys Ile Tyr Asp Tyr Leu Met His Ser Leu
                405                 410                 415
Ile His Phe Gln Gly Phe Phe Val Ala Thr Ile Tyr Cys Phe Cys Asn
            420                 425                 430
His Glu Val Gln Val Thr Leu Lys Arg Gln Trp Thr Gln Phe Lys Ile
        435                 440                 445
Gln Trp Ser Gln Arg Trp Gly Arg Arg Arg Pro Thr Asn Arg Val
    450                 455                 460
Val Ser Ala Pro Arg Ala Val Ala Phe Ala Glu Pro Asp Gly Leu Pro
465                 470                 475                 480
Ile Tyr Ile Cys His Gln Glu Pro Arg Asn Pro Ile Ser Asn Asn
                485                 490                 495
Glu Gly Glu Glu Ser Thr Glu Met Ile Pro Met Asn Val Ile Gln Gln
            500                 505                 510
Asp Ala Ser Ala
        515

<210> SEQ ID NO 3
<211> LENGTH: 469
<212> TYPE: PRT
<213> ORGANISM: Gallus gallus

<400> SEQUENCE: 3

Met Lys Lys Thr Thr His Ser Cys Phe Leu Leu Ile Ile Leu Leu Ile
1               5                   10                  15
Arg Met Val Pro Ser Leu Thr Ala Thr Val Asn Tyr Thr Asp Pro Thr
            20                  25                  30
Leu Glu Pro Val Val Thr Glu Asn Ser Val Ile Arg Gln Lys Ile Ile
        35                  40                  45
Asp Ser Gln Phe Lys Cys Tyr Glu Arg Met Asn Arg Ala Pro Pro Tyr
    50                  55                  60
Arg Lys Lys Gly Leu Phe Cys Asn Arg Thr Trp Asp Gly Trp Leu Cys
65                  70                  75                  80
Trp Asp Asp Thr Pro Ala Gly Arg Ile Thr Ala Gln Asn Cys Pro Asp
                85                  90                  95
Tyr Phe Pro Asp Phe Asp Pro Thr Glu Arg Ala Ser Lys Tyr Cys Asp
            100                 105                 110
Glu Thr Gly Asn Trp Phe Arg His Pro Glu Ser Asn Arg Thr Trp Ser
        115                 120                 125
Asn Tyr Thr Leu Cys Asn Ser Phe Thr Ser Glu Lys Leu Lys Met Ala
    130                 135                 140
Phe Ile Leu Tyr Tyr Met Ala Ile Val Gly His Ala Leu Ser Ile Thr
145                 150                 155                 160
Ser Leu Leu Ile Ser Leu Ala Ile Phe Phe Tyr Phe Lys Ser Leu Ser
                165                 170                 175
Cys Gln Arg Ile Thr Leu His Lys Asn Leu Phe Phe Ser Tyr Val Leu
            180                 185                 190
Asn Ser Met Phe Thr Ile Ala His Leu Ile Ile Val Val Pro Asn Pro
        195                 200                 205
```

Gly Leu Val Lys Arg Asp Pro Val Ser Cys Lys Val Leu Gln Phe Phe
210                 215                 220

His Gln Tyr Met Leu Gly Cys Asn Tyr Phe Trp Met Leu Cys Glu Gly
225                 230                 235                 240

Ile Tyr Leu His Thr Leu Ile Val Val Ala Val Phe Ala Glu Glu Gln
            245                 250                 255

Arg Leu His Trp Tyr Tyr Leu Leu Gly Trp Gly Phe Pro Leu Val Pro
            260                 265                 270

Ala Ser Ile His Ala Val Ala Arg Ala Lys Tyr Phe Asn Asp Asn Cys
            275                 280                 285

Trp Met Ser Val Asp Thr His Leu Leu Tyr Ile Val His Gly Pro Val
290                 295                 300

Met Ala Ala Leu Leu Val Asn Phe Phe Phe Leu Leu Asn Ile Val Arg
305                 310                 315                 320

Val Leu Val Thr Lys Leu Arg Asp Thr His Arg Ala Glu Ser Asn Met
            325                 330                 335

Tyr Met Lys Ala Val Arg Ala Thr Leu Ile Leu Val Pro Leu Leu Gly
            340                 345                 350

Ile Gln Phe Val Ile Pro Trp Arg Pro Glu Asn Arg Leu Ala Gly
            355                 360                 365

Glu Ile Tyr Asp Tyr Ile Met His Ile Leu Met His Tyr Gln Gly Leu
370                 375                 380

Leu Val Ala Thr Ile Phe Cys Phe Phe Asn Gly Glu Val Gln Gly Ala
385                 390                 395                 400

Leu Lys Arg Gln Trp Thr Gln Tyr Lys Thr Gln Trp Gly Gln Arg Arg
            405                 410                 415

Arg Glu His Cys Ser Thr Arg Ser Thr Ser Tyr Thr Ala Thr Ser Ile
            420                 425                 430

Thr Glu Val Pro Val Tyr Leu Tyr His His Asp Ser Asn Asn Glu Gln
            435                 440                 445

Leu Asn Gly Arg Tyr Val Asp Asp Ser Glu Leu Val Ala Leu Lys Ser
            450                 455                 460

Gly Glu Thr Ser Ala
465

<210> SEQ ID NO 4
<211> LENGTH: 794
<212> TYPE: PRT
<213> ORGANISM: Takifugu rupripes

<400> SEQUENCE: 4

Met Lys Ser Ala Gly Tyr Ser Cys Ile Leu Trp Leu Leu Leu Met Met
1               5                   10                  15

Val Thr Asp Thr Glu Ser Leu Ser Glu Pro Ser Leu Ser Pro Gly Gln
            20                  25                  30

Ser Leu Thr Trp Arg Gln Lys Lys Cys Asp Glu Met Ser Asn Lys Arg
            35                  40                  45

Pro Gly Asn Arg Thr Gly Met Phe Cys Ala His Phe Trp Asp Gly Phe
        50                  55                  60

Leu Cys Trp Glu Glu Thr Pro Ala Gly Glu Ser Val Thr Lys Thr Cys
65                  70                  75                  80

Pro Asp His Pro Glu Leu Asp Ser Ala Glu Lys Val Thr Lys Tyr Cys
            85                  90                  95

Asp Ser Leu Gly Asn Trp Ile Gln Thr Gly Ser Thr Cys Gln Pro Ala

```
            100                 105                 110
Ser Arg His Thr Leu Thr Leu Leu Met Asp Ala Pro Thr Glu Pro Arg
            115                 120                 125

Thr Glu Glu Thr Gly Glu Lys Gly Ala Ile Val Glu Leu Leu Leu Glu
            130                 135                 140

Asn Glu Lys Thr Cys Tyr Glu Lys Met Lys Arg Asn Pro Pro Tyr Asn
145                 150                 155                 160

Gly Thr Gly Gly Leu Phe Cys Gly Arg Asn Trp Asp Gly Trp Leu Cys
                    165                 170                 175

Trp Asp Asp Thr Pro Ala Gly Thr Tyr Thr Ser Gln Asn Cys Pro Glu
                180                 185                 190

Phe Phe Ser Glu Phe Glu Gln Pro Gly Lys Ala Thr Lys Phe Cys Gly
            195                 200                 205

Glu Asp Gly Arg Trp Phe Arg His Pro Glu Thr Asn Arg Ile Trp Thr
            210                 215                 220

Asn Tyr Thr Leu Cys Ala Ser Thr Gln Glu Lys Arg Leu Lys Lys Leu
225                 230                 235                 240

Lys Leu Leu Glu Asn Glu Tyr Lys Cys Leu Leu Lys Met Asn Arg Glu
                    245                 250                 255

Ala Ser Gly Asn Lys Ser Gly Ser Tyr Cys Ser Arg Asn Trp Asp Gly
                260                 265                 270

Trp Leu Cys Trp Asp Asp Thr Gln Ala Gly Thr Val Ala Ser Gln Asn
            275                 280                 285

Cys Pro Asp Tyr Phe Phe Asn Thr Asp Pro Thr Glu Lys Ala Thr Lys
            290                 295                 300

Tyr Cys Gly Glu Asp Ser Gln Trp Phe Arg His Pro Glu Thr Asn Arg
305                 310                 315                 320

Met Trp Thr Asn Tyr Ser Leu Cys Ser Val Ser Asn Lys Glu Met Leu
                    325                 330                 335

Lys Ala Ala Ala Gln Phe Ser Ala Asp Leu Glu Val Asp Pro Ser Asp
                340                 345                 350

Glu Ala Thr Val Ser Pro Met Val Asn Pro Glu Glu Gln Glu Met Val
            355                 360                 365

Arg Lys Lys Ile Leu Asp Ser Gln Tyr Lys Cys Phe Glu Lys Met Asn
            370                 375                 380

Arg Gln Pro Pro Tyr Asn Lys Thr Ala Pro Tyr Cys Ser Arg Asn Trp
385                 390                 395                 400

Asp Gly Trp Leu Cys Trp Asp Asp Thr Pro Ala Ala Thr Tyr Ala Ser
                    405                 410                 415

Gln Asn Cys Pro Asn Tyr Phe Val Asp Phe Asp Pro Thr Glu Lys Ala
                420                 425                 430

Thr Lys Tyr Cys Gly Glu Asp Gly Gln Trp Phe Arg His Pro Asp Thr
            435                 440                 445

Asn Arg Thr Trp Ser Asn Tyr Thr Leu Cys Asn Glu Asn Thr Lys Ala
            450                 455                 460

Lys Leu Lys Ser Ala Tyr Ile Leu Phe Tyr Met Ala Ile Val Gly His
465                 470                 475                 480

Ala Leu Ser Ile Ala Ser Leu Leu Ile Ser Leu Ala Ile Phe Phe Tyr
                    485                 490                 495

Phe Arg Ser Leu Ser Cys Gln Arg Ile Thr Leu His Lys Asn Leu Phe
                500                 505                 510

Cys Ser Tyr Val Leu Asn Ser Ala Leu Thr Ile Ile Tyr Leu Val Ala
            515                 520                 525
```

Val Val Asn Asn Pro Glu Val Ser Arg Asn Pro Val Gly Cys Lys
        530                 535                 540

Val Leu His Phe Phe His Met Tyr Met Leu Gly Cys Asn Tyr Phe Trp
545                 550                 555                 560

Met Leu Cys Glu Gly Ile Tyr Leu His Thr Leu Ile Val Ala Val
                565                 570                 575

Phe Ala Glu Glu Gln His Leu His Trp Tyr Tyr Leu Gly Trp Gly
            580                 585                 590

Phe Pro Leu Val Pro Ala Ser Ile His Ala Val Ala Arg Lys Lys Tyr
            595                 600                 605

Phe Asp Asp Asn Cys Trp Met Ser Val Glu Thr His Leu Leu Tyr Ala
    610                 615                 620

Val His Gly Pro Ile Val Ala Ala Leu Leu Val Asn Leu Phe Phe Leu
625                 630                 635                 640

Leu Asn Ile Ile Arg Val Leu Val Thr Lys Leu Arg Asp Thr His Arg
                645                 650                 655

Ala Glu Ser Asn Met Tyr Met Lys Ala Val Arg Ala Thr Leu Ile Leu
            660                 665                 670

Val Pro Leu Leu Gly Ile Gln Phe Val Ile Phe Pro Trp Arg Pro Glu
            675                 680                 685

Asn Arg Ile Ala Gly Glu Val Tyr Glu Tyr Ile Met His Ile Leu Met
    690                 695                 700

His Tyr Gln Gly Leu Leu Val Ala Thr Ile Phe Cys Phe Phe Asn Gly
705                 710                 715                 720

Glu Val Gln Ala Ala Leu Lys Arg Gln Trp Met Gln Tyr Lys Thr Gln
                725                 730                 735

Trp Gly Gln Arg Arg Lys Asp His Cys Ser Met Arg Ser Thr Ser Tyr
            740                 745                 750

Thr Ala Thr Ser Ile Thr Glu Val Pro Thr Phe Met Tyr His His Glu
            755                 760                 765

Cys Asn Ser Glu His Leu Asn Gly Arg His Thr Glu Asp Ser Glu Leu
    770                 775                 780

Val Ala Leu Lys Thr Gly Glu Thr Tyr Ala
785                 790

<210> SEQ ID NO 5
<211> LENGTH: 546
<212> TYPE: PRT
<213> ORGANISM: Caenorhabditis elegans

<400> SEQUENCE: 5

Met Ala Asp Ala Thr Ser Pro Phe Asn Val Ser Ile Leu Asp Asn Ser
1               5                   10                  15

Thr Lys Leu Ser Glu Met Val Glu Ser Gly Trp Asn Val Leu Ala Ser
                20                  25                  30

Thr Ser Val Gln Ala Phe Asn Glu Ala Met Asp Val Leu Glu Glu Ser
            35                  40                  45

Tyr Pro Leu Cys Lys Lys Met Leu Asp His Asn Asn Leu Phe Pro Glu
        50                  55                  60

Arg Asp Pro Asn Asp Thr Arg Ile Trp Cys Asn Ala Thr Tyr Asp Thr
65                  70                  75                  80

Val Leu Cys Trp Pro Thr Pro Ala Asn Ser Ser Val Thr Leu Gln
                85                  90                  95

Cys Pro His Met Lys Gly Leu Asp Pro Asn Lys Asn Ile Thr Lys Asp

```
                100              105              110
        Cys His Val Ser Gly Val Trp Ser Gly Arg Asn Ala Gly Glu Met Gly
                    115              120              125
        Pro Thr Leu Pro Gly Trp Thr Asn Phe Thr Met Cys Tyr Thr Asp Glu
                    130              135              140
        Val Ile Tyr Ile Met Gln Asn Leu Asn Asn Glu Ser Leu Thr Ile Ala
        145              150              155              160
        Gln Glu Val Ala Arg Asn Ala Arg Lys Leu Glu Phe Val Gly Leu Gly
                    165              170              175
        Leu Ser Leu Val Ser Leu Ile Leu Ala Ile Ser Ile Phe Ser Tyr Phe
                    180              185              190
        Arg Arg Leu Arg Val Phe Arg Asn Leu Leu His Leu His Leu Met Ile
                    195              200              205
        Ala Met Leu Met Val Val Ile Leu Arg Leu Val Leu Tyr Ile Asp Leu
        210              215              220
        Ile Phe Thr Gly Glu Asn Gly Pro His Thr Asn Ser Ala Glu Gly Lys
        225              230              235              240
        Thr Ile Asn Thr Met Pro Ile Val Cys Glu Gly Met Phe Phe Phe Leu
                    245              250              255
        Glu Tyr Phe Lys Thr Val Thr Phe Cys Trp Met Phe Leu Glu Gly Ile
                    260              265              270
        Tyr Leu Asn Asn Gln Ile Val Phe Gly Phe Phe Asn Ser Glu Pro Lys
                    275              280              285
        Leu Leu Pro Tyr Phe Ile Ala Gly Tyr Gly Ile Pro Leu Val His Thr
        290              295              300
        Met Leu Trp Leu Leu Val Val Leu Ile Lys Lys Asp Phe Lys Val Glu
        305              310              315              320
        Arg Cys Leu Gly Ser Tyr Tyr Leu Glu Pro Glu Phe Trp Ile Leu Asp
                    325              330              335
        Gly Pro Arg Met Ala Glu Leu Val Ile Asn Leu Phe Phe Ile Cys Asn
                    340              345              350
        Val Ile Arg Val Leu Tyr Ser Lys Val Arg Glu Ser Asn Asn Thr Ser
                    355              360              365
        Glu Ala Gly Leu Lys Lys Ser Val Lys Ala Ala Met Met Leu Leu Pro
                    370              375              380
        Leu Leu Gly Val Pro Asn Ile Met Gln Thr Ile Pro Phe Ala Pro Thr
        385              390              395              400
        Arg Asp Asn Ile Met Val Phe Ala Val Trp Thr Tyr Thr Ala Ser Phe
                    405              410              415
        Thr Tyr Met Tyr Gln Gly Leu Met Val Ala Ser Ile Tyr Cys Phe Thr
                    420              425              430
        Asn Lys Glu Val Asn His Val Leu Lys Thr Phe Tyr Ala Arg Tyr Arg
                    435              440              445
        Leu Leu His Lys Ser Gln Asn Glu Leu Arg Arg Gly Ser Arg Ser Val
                    450              455              460
        Ala Ser His Tyr Ala Ala Lys Asn Gly Thr Ala Asn Ala Ser Ala Pro
        465              470              475              480
        Gln Thr Asn Asn Ala Asp Glu Phe Gly Lys Leu Ser Pro Phe Pro Ser
                    485              490              495
        Arg Ser Lys Lys Gly Ser Asp Asp Ser Thr Thr Lys Leu Met Lys Asp
                    500              505              510
        Ala Val Met Glu Glu Glu Lys Asn Ala Asn Asn Asn Gly Tyr Gly Ser
                    515              520              525
```

```
Ala Gly Glu Met Thr Pro Leu Arg Glu Gly Ser Asn Arg Ser Thr Lys
        530                 535                 540

Ser Pro
545

<210> SEQ ID NO 6
<211> LENGTH: 18
<212> TYPE: PRT
<213> ORGANISM: Artificial
<220> FEATURE:
<223> OTHER INFORMATION: Homo sapiens epitope

<400> SEQUENCE: 6

Asp Pro Ser Glu Lys Val Thr Lys Tyr Cys Asp Glu Lys Gly Val Trp
1               5                   10                  15

Phe Lys

<210> SEQ ID NO 7
<211> LENGTH: 18
<212> TYPE: PRT
<213> ORGANISM: Artificial
<220> FEATURE:
<223> OTHER INFORMATION: Mus musculus epitope

<400> SEQUENCE: 7

Asp Thr Ala Glu Lys Val Ser Lys Tyr Cys Asp Glu Asn Gly Glu Trp
1               5                   10                  15

Phe Arg

<210> SEQ ID NO 8
<211> LENGTH: 18
<212> TYPE: PRT
<213> ORGANISM: Artificial
<220> FEATURE:
<223> OTHER INFORMATION: Gallus gallus epitope

<400> SEQUENCE: 8

Asp Pro Thr Glu Arg Ala Ser Lys Tyr Cys Asp Glu Thr Gly Asn Trp
1               5                   10                  15

Phe Arg

<210> SEQ ID NO 9
<211> LENGTH: 18
<212> TYPE: PRT
<213> ORGANISM: Artificial
<220> FEATURE:
<223> OTHER INFORMATION: Fish epitope

<400> SEQUENCE: 9

Asp Ser Ala Glu Lys Val Thr Lys Tyr Cys Asp Ser Leu Gly Asn Trp
1               5                   10                  15

Ile Gln

<210> SEQ ID NO 10
<211> LENGTH: 18
<212> TYPE: PRT
<213> ORGANISM: Artificial
<220> FEATURE:
<223> OTHER INFORMATION: Fish epitope

<400> SEQUENCE: 10

Asp Pro Thr Glu Lys Ala Thr Lys Tyr Cys Gly Glu Asp Ser Gln Trp
1               5                   10                  15
```

Phe Arg

```
<210> SEQ ID NO 11
<211> LENGTH: 18
<212> TYPE: PRT
<213> ORGANISM: Artificial
<220> FEATURE:
<223> OTHER INFORMATION: Fish epitope

<400> SEQUENCE: 11
```

Asp Pro Thr Glu Lys Ala Thr Lys Tyr Cys Gly Glu Asp Gly Gln Trp
1               5                   10                  15

Phe Arg

```
<210> SEQ ID NO 12
<211> LENGTH: 18
<212> TYPE: PRT
<213> ORGANISM: Artificial
<220> FEATURE:
<223> OTHER INFORMATION: C. elegans epitope

<400> SEQUENCE: 12
```

Asp Pro Asn Lys Asn Ile Thr Lys Asp Cys His Val Ser Gly Val Trp
1               5                   10                  15

Ser Gly

```
<210> SEQ ID NO 13
<211> LENGTH: 32
<212> TYPE: PRT
<213> ORGANISM: Artificial
<220> FEATURE:
<223> OTHER INFORMATION: Amino acid sequence of calcitonin

<400> SEQUENCE: 13
```

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

```
<210> SEQ ID NO 14
<211> LENGTH: 32
<212> TYPE: PRT
<213> ORGANISM: Artificial
<220> FEATURE:
<223> OTHER INFORMATION: Salmon calcitonin

<400> SEQUENCE: 14
```

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

```
<210> SEQ ID NO 15
<211> LENGTH: 25
<212> TYPE: PRT
<213> ORGANISM: Artificial
<220> FEATURE:
<223> OTHER INFORMATION: Salmon calcitonin 8-32

<400> SEQUENCE: 15
```

Val Leu Gly Lys Leu Ser Gln Glu Leu His Lys Leu Gln Thr Tyr Pro
1               5                   10                  15

Arg Thr Asn Thr Gly Ser Gly Thr Pro

-continued

```
                20                  25

<210> SEQ ID NO 16
<211> LENGTH: 114
<212> TYPE: PRT
<213> ORGANISM: Artificial
<220> FEATURE:
<223> OTHER INFORMATION: 2C4 VH sequence

<400> SEQUENCE: 16

Gln Val His Leu Gln Gln Ser Gly Ala Glu Leu Ala Arg Pro Gly Ala
1               5                   10                  15

Ser Val Arg Leu Ser Cys Glu Ala Ser Gly Tyr Thr Phe Thr Lys Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asp Gly Asp Ser Arg Tyr Thr Pro Lys Phe
    50                  55                  60

Lys Gly Lys Ala Thr Leu Thr Ala Asp Lys Ser Ser Gly Thr Ala Tyr
65                  70                  75                  80

Ile Gln Leu Ser Ser Leu Ala Ser Glu Asp Ser Ala Val Tyr Tyr Cys
                85                  90                  95

Ala Arg Gly Asp Gly Thr Tyr Trp Gly Gln Gly Thr Leu Val Thr Val
                100                 105                 110

Ser Ala

<210> SEQ ID NO 17
<211> LENGTH: 113
<212> TYPE: PRT
<213> ORGANISM: Artificial
<220> FEATURE:
<223> OTHER INFORMATION: 6G11/10D1 VH sequence

<400> SEQUENCE: 17

Gln Val Gln Leu Gln Gln Ser Gly Ala Asp Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Asp Gly Leu Tyr Trp Gly Gln Gly Thr Leu Thr Val
                100                 105                 110

Ser

<210> SEQ ID NO 18
<211> LENGTH: 113
<212> TYPE: PRT
<213> ORGANISM: Artificial Sequence
<220> FEATURE:
<223> OTHER INFORMATION: 9B4 VH sequence

<400> SEQUENCE: 18

Gln Val Gln Leu Gln Gln Ser Gly Ala Glu Leu Ala Arg Pro Gly Ala
```

```
1               5                   10                  15
Ser Val Lys Leu Ser Cys Lys Ala Ser Gly Tyr Thr Phe Thr Ser Tyr
                20                  25                  30

Trp Ile Gln Trp Val Lys Gln Arg Pro Gly Gln Gly Leu Glu Trp Ile
                35                  40                  45

Gly Ala Ile Tyr Pro Gly Asp Asp Thr Arg Tyr Thr Gln Lys Phe
 50                  55                  60

Lys Gly Lys Ala Thr Leu Thr Ala Asp Lys Ser Ala Ser Thr Gly Tyr
65                   70                  75                  80

Met Gln Leu Ser Ser Leu Ala Ser Glu Asp Ser Ala Val Tyr Tyr Cys
                85                  90                  95

Ala Arg Gly Asp Gly Leu Tyr Trp Gly Gln Gly Thr Pro Leu Thr Val
                100                 105                 110

Ser
```

<210> SEQ ID NO 19
<211> LENGTH: 107
<212> TYPE: PRT
<213> ORGANISM: Artificial Sequence
<220> FEATURE:
<223> OTHER INFORMATION: 2C4 VL sequence

<400> SEQUENCE: 19

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
                35                  40                  45

Tyr Lys Ala Lys Thr Leu Glu Glu Gly Val Pro Ser Arg Phe Ser Gly
                50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Arg
                85                  90                  95

Thr Phe Gly Gly Gly Thr Lys Leu Glu Ile Lys
                100                 105
```

<210> SEQ ID NO 20
<211> LENGTH: 107
<212> TYPE: PRT
<213> ORGANISM: Artificial Sequence
<220> FEATURE:
<223> OTHER INFORMATION: 6G11/10D1 VL sequence

<400> SEQUENCE: 20

```
Asp Ile Gln Met Thr Gln Ser Pro Ala Ser Leu Ser Ala Ser Val Gly
1               5                   10                  15

Glu Thr Val Thr Ile Thr Cys Arg Ser Ser Glu Asn Ile Tyr Ser Tyr
                20                  25                  30

Leu Ala Trp Tyr Gln Gln Lys Gln Gly Lys Ser Pro Gln Leu Leu Val
                35                  40                  45

Tyr Thr Ala Lys Thr Leu Ala Glu Gly Val Pro Ser Arg Phe Ser Gly
                50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Arg
```

```
                    85                  90                  95

Thr Phe Gly Gly Gly Thr Lys Leu Glu Ile Lys
                100                 105

<210> SEQ ID NO 21
<211> LENGTH: 107
<212> TYPE: PRT
<213> ORGANISM: Artificial Sequence
<220> FEATURE:
<223> OTHER INFORMATION: 9B4 VL sequence

<400> SEQUENCE: 21

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Arg Lys Ser Pro Gln Leu Leu Val
        35                  40                  45

Tyr Leu Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Arg
                85                  90                  95

Thr Phe Gly Gly Gly Thr Lys Leu Glu Ile Lys
                100                 105

<210> SEQ ID NO 22
<211> LENGTH: 7
<212> TYPE: PRT
<213> ORGANISM: Artificial Sequence
<220> FEATURE:
<223> OTHER INFORMATION: 2C4 CDR H1 Chothia/AbM

<400> SEQUENCE: 22

Gly Tyr Thr Phe Thr Lys Tyr
1               5

<210> SEQ ID NO 23
<211> LENGTH: 10
<212> TYPE: PRT
<213> ORGANISM: Artificial Sequence
<220> FEATURE:
<223> OTHER INFORMATION: 2C4 CDR H2 Chothia/AbM

<400> SEQUENCE: 23

Ala Ile Tyr Pro Gly Asp Gly Asp Ser Arg
1               5                   10

<210> SEQ ID NO 24
<211> LENGTH: 5
<212> TYPE: PRT
<213> ORGANISM: Artificial Sequence
<220> FEATURE:
<223> OTHER INFORMATION: 2C4 CDR H3 Chothia/AbM

<400> SEQUENCE: 24

Gly Asp Gly Thr Tyr
1               5

<210> SEQ ID NO 25
<211> LENGTH: 5
<212> TYPE: PRT
```

```
<213> ORGANISM: Artificial Sequence
<220> FEATURE:
<223> OTHER INFORMATION: 2C4 CDR H1 Kabat

<400> SEQUENCE: 25

Lys Tyr Trp Met Gln
1               5

<210> SEQ ID NO 26
<211> LENGTH: 17
<212> TYPE: PRT
<213> ORGANISM: Artificial Sequence
<220> FEATURE:
<223> OTHER INFORMATION: 2C4 CDR H2 Kabat

<400> SEQUENCE: 26

Ala Ile Tyr Pro Gly Asp Gly Asp Ser Arg Tyr Thr Pro Lys Phe Lys
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: 2C4 CDR L1

<400> SEQUENCE: 27

Arg Ala Ser Glu Asn Ile Tyr Ser Tyr Leu Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: 2C4 CDR L2

<400> SEQUENCE: 28

Lys Ala Lys Thr Leu Glu Glu
1               5

<210> SEQ ID NO 29
<211> LENGTH: 9
<212> TYPE: PRT
<213> ORGANISM: Artificial Sequence
<220> FEATURE:
<223> OTHER INFORMATION: 2C4 CDR L3

<400> SEQUENCE: 29

Gln His His Tyr Gly Thr Pro Arg Thr
1               5

<210> SEQ ID NO 30
<211> LENGTH: 7
<212> TYPE: PRT
<213> ORGANISM: Artificial Sequence
<220> FEATURE:
<223> OTHER INFORMATION: 6G11/10D1 CDR H1 Chothia/AbM

<400> SEQUENCE: 30

Gly Tyr Thr Phe Thr Ser Tyr
1               5

<210> SEQ ID NO 31
<211> LENGTH: 10
```

```
<212> TYPE: PRT
<213> ORGANISM: Artificial Sequence
<220> FEATURE:
<223> OTHER INFORMATION: 6G11/10D1 CDR H2 Chothia/AbM

<400> SEQUENCE: 31

Ala Ile Tyr Pro Gly Asp Gly Asp Thr Arg
1               5                   10

<210> SEQ ID NO 32
<211> LENGTH: 5
<212> TYPE: PRT
<213> ORGANISM: Artificial Sequence
<220> FEATURE:
<223> OTHER INFORMATION: 6G11/10D1 CDR H3 Chothia/AbM

<400> SEQUENCE: 32

Gly Asp Gly Leu Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: 6G11/10D1 HDR H1 Kabat

<400> SEQUENCE: 33

Ser Tyr Trp Met Gln
1               5

<210> SEQ ID NO 34
<211> LENGTH: 17
<212> TYPE: PRT
<213> ORGANISM: Artificial Sequence
<220> FEATURE:
<223> OTHER INFORMATION: 6G11/10D1 CDR H2 Kabat

<400> SEQUENCE: 34

Ala Ile Tyr Pro Gly Asp Gly Asp Thr Arg Tyr Thr Gln Lys Phe Lys
1               5                   10                  15

Gly

<210> SEQ ID NO 35
<211> LENGTH: 11
<212> TYPE: PRT
<213> ORGANISM: Artificial Sequence
<220> FEATURE:
<223> OTHER INFORMATION: 6G11/10D1 CDR L1

<400> SEQUENCE: 35

Arg Ser Ser Glu Asn Ile Tyr Ser Tyr Leu Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: 6G11/10D1 CDR L2

<400> SEQUENCE: 36

Thr Ala Lys Thr Leu Ala Glu
1               5

<210> SEQ ID NO 37
```

```
<211> LENGTH: 9
<212> TYPE: PRT
<213> ORGANISM: Artificial Sequence
<220> FEATURE:
<223> OTHER INFORMATION: 6G11/10D1 CDR L3

<400> SEQUENCE: 37

Gln His His Tyr Gly Thr Pro Arg Thr
1               5

<210> SEQ ID NO 38
<211> LENGTH: 7
<212> TYPE: PRT
<213> ORGANISM: Artificial Sequence
<220> FEATURE:
<223> OTHER INFORMATION: 9B4 CDR H1 Chothia/AbM

<400> SEQUENCE: 38

Gly Tyr Thr Phe Thr Ser Tyr
1               5

<210> SEQ ID NO 39
<211> LENGTH: 10
<212> TYPE: PRT
<213> ORGANISM: Artificial Sequence
<220> FEATURE:
<223> OTHER INFORMATION: 9B4 CDR H3 Chothia/AbM

<400> SEQUENCE: 39

Ala Ile Tyr Pro Gly Asp Asp Asp Thr Arg
1               5                   10

<210> SEQ ID NO 40
<211> LENGTH: 5
<212> TYPE: PRT
<213> ORGANISM: Artificial Sequence
<220> FEATURE:
<223> OTHER INFORMATION: 9B4 CDR H3 Chothia/AbM

<400> SEQUENCE: 40

Gly Asp Gly Leu Tyr
1               5

<210> SEQ ID NO 41
<211> LENGTH: 5
<212> TYPE: PRT
<213> ORGANISM: Artificial Sequence
<220> FEATURE:
<223> OTHER INFORMATION: 9B4 CDR H1 Kabat

<400> SEQUENCE: 41

Ser Tyr Trp Ile Gln
1               5

<210> SEQ ID NO 42
<211> LENGTH: 17
<212> TYPE: PRT
<213> ORGANISM: Artificial Sequence
<220> FEATURE:
<223> OTHER INFORMATION: 9B4 CDR H2 Kabat

<400> SEQUENCE: 42

Ala Ile Tyr Pro Gly Asp Asp Asp Thr Arg Tyr Thr Gln Lys Phe Lys
1               5                   10                  15

Gly
```

<210> SEQ ID NO 43
<211> LENGTH: 11
<212> TYPE: PRT
<213> ORGANISM: Artificial Sequence
<220> FEATURE:
<223> OTHER INFORMATION: 9B4 CDR L1

<400> SEQUENCE: 43

Arg Ala Ser Glu Asn Ile Tyr Ser Tyr Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: 9B4 CDR L2

<400> SEQUENCE: 44

Leu Ala Lys Thr Leu Ala Glu
1               5

<210> SEQ ID NO 45
<211> LENGTH: 9
<212> TYPE: PRT
<213> ORGANISM: Artificial Sequence
<220> FEATURE:
<223> OTHER INFORMATION: 9B4 CDR L3

<400> SEQUENCE: 45

Gln His His Tyr Gly Thr Pro Arg Thr
1               5

<210> SEQ ID NO 46
<211> LENGTH: 342
<212> TYPE: DNA
<213> ORGANISM: Artificial Sequence
<220> FEATURE:
<223> OTHER INFORMATION: 2C4 VH

<400> SEQUENCE: 46
caggttcatc tccagcagtc tggggctgag ctggcaagac ctggggcttc agtgaggttg      60
tcctgcgagg cttctggcta cacctttact aaatactgga tgcagtggat aaaacagagg     120
cctggacagg gtctagaatg gattggggct atttatcctg agatggtga ttctaggtac      180 actccgaaat tcaagggcaa ggccacattg actgcagata atcttccgg cacagcctac      240 atacaactca gtagtttggc atctgaggac tctgcggtct attactgtgc aagaggggac     300
ggtacttact ggggccaagg gactctggtc actgtctctg ca                        342

<210> SEQ ID NO 47
<211> LENGTH: 321
<212> TYPE: DNA
<213> ORGANISM: Artificial Sequence
<220> FEATURE:
<223> OTHER INFORMATION: 2C4 VL

<400> SEQUENCE: 47
gacatccaga tgactcagtc tccagcctcc ctatctgcat ctgtgggaga aactgtcacc      60
atcacatgtc gagcaagtga aaatatttat agttatttag catggtatca gcagaaacag     120
ggaaaatctc ctcagctcct ggtctataaa gcaaaaacct tagaagaagg tgtgccatca     180
aggttcagtg gcagtggatc aggcacacag ttttctctga agatcaacag cctgcagcct     240
gaagattttg ggagttatta ctgtcaacat cattatggaa ctcctcggac gttcggtgga     300
ggcaccaaac tggaaatcaa a                                              321

<210> SEQ ID NO 48
<211> LENGTH: 339
<212> TYPE: DNA
<213> ORGANISM: Artificial Sequence
<220> FEATURE:
<223> OTHER INFORMATION: 6G11/10D1 VH

<400> SEQUENCE: 48
caggttcagc tccagcagtc tggggctgac ctggcaagac ctggggcttc agtgaagttg     60
tcctgcaagg cttctggcta cacctttact agttactgga tgcagtgggt aaaacagagg    120
cctggacagg gtctggaatg gattgggget atttatcctg agatggtga tactaggtac    180 actcagaagt tcaagggcaa ggccacattg actgcagata atcctccac cacagcctac    240 atgcaactca gcagcttggc atctgaggac tctgcggtct attactgtgc aagagggat    300 ggtctttatt ggggccaagg caccactctc acagtctcc                           339

<210> SEQ ID NO 49
<211> LENGTH: 321
<212> TYPE: DNA
<213> ORGANISM: Artificial Sequence
<220> FEATURE:
<223> OTHER INFORMATION: 6G11/10D1 VL

<400> SEQUENCE: 49
gacatccaga tgactcagtc tccagcctcc ctatctgcat ctgtgggaga aactgtcacc     60
ataacatgtc gatcaagtga aaatatttac agttatttag catggtatca gcagaaacag    120
ggaaaatctc ctcagctcct ggtctatact gcaaaaacct tagcagaagg tgtgccatca    180
aggttcagtg gcagtggatc aggcacacag ttttctctga agatcaatag cctgcagcct    240
gaagattttg ggagttatta ctgtcaacat cattatggaa ctcctcggac gttcggtgga    300
ggcaccaagc tggaaatcaa a                                              321

<210> SEQ ID NO 50
<211> LENGTH: 339
<212> TYPE: DNA
<213> ORGANISM: Artificial Sequence
<220> FEATURE:
<223> OTHER INFORMATION: 9B4 VH

<400> SEQUENCE: 50
caggttcaac tccagcagtc tggggctgag ctggcaagac ctggggcttc agtgaagttg     60
tcctgcaagg cttctggcta cacctttact agctactgga tacagtgggt aaaacagagg    120
cctggacagg gtctggaatg gattgggget atttatcctg agatgatga tactaggtac    180 actcagaagt tcaagggcaa ggccacattg actgcagata atcagccag cacaggctac    240 atgcaactca gcagcttggc atctgaggac tctgcggtct attactgtgc aagagggat    300 ggtctttact ggggccaagg cacccctctc acagtctcc                           339

<210> SEQ ID NO 51
<211> LENGTH: 321
<212> TYPE: DNA
<213> ORGANISM: Artificial Sequence
<220> FEATURE:
<223> OTHER INFORMATION: 9B4 VL

<400> SEQUENCE: 51

```
gacatccaga tgactcagtc tccagcctcc ctatctgcat ctgtgggaga aactgtcacc    60
atcacatgtc gagcaagtga aatatttac agttatttag catggtatca gcagaaacag    120
agaaaatctc ctcagctcct ggtctatctt gcaaaaacct agcagaagg tgtgccatca    180 aggttcagtg gcagtggatc aggcacacag ttttctctga agatcaacag cctgcagcct    240
gaagattttg ggagttatta ctgtcaacat cattatggta ctcctcggac gttcggtgga    300
ggcaccaagc tggaaatcaa a                                             321
```

<210> SEQ ID NO 52
<211> LENGTH: 410
<212> TYPE: PRT
<213> ORGANISM: Culex quinquefasciatus

<400> SEQUENCE: 52

```
Met Ser Ser Ser Thr Thr Thr Glu Ala Ser Val Asp Val Ser Glu Leu
1               5                   10                  15

Lys Arg Leu Glu Cys Leu Ala Lys Leu Asn Glu Ser Val Glu Ser Ala
            20                  25                  30

Ser Asp Ser Asp Gln Leu Phe Cys Arg Gly Thr Trp Asp Gly Trp Gln
        35                  40                  45

Cys Trp Pro Asp Thr Ala Ala Gly Arg Ile Ala Tyr Ala Pro Cys Pro
    50                  55                  60

Glu Phe Val Phe Gly Phe Asp Thr Thr Arg Phe Ala His Lys Ala Cys
65                  70                  75                  80

Asp Glu Gln Gly Glu Trp Phe Arg His Pro Glu Thr Asn Arg Thr Trp
                85                  90                  95

Ser Asn Tyr Thr Thr Cys Val Asn Ile Asp Asp Phe Thr Trp Ser Arg
            100                 105                 110

Gln Ile Asn Thr Ile Tyr Glu Thr Gly Tyr Ser Ile Ser Leu Ile Ala
        115                 120                 125

Leu Ile Leu Ser Leu Gly Ile Leu Ser Tyr Phe Arg Ser Leu Lys Cys
    130                 135                 140

Ala Arg Ile Thr Leu His Met Asn Leu Phe Ala Ser Phe Ala Thr Asn
145                 150                 155                 160

Asn Thr Leu Trp Leu Leu Trp Tyr Arg Met Val Leu Ala Asp Pro Glu
                165                 170                 175

Val Leu Ser His Asn Gly Ser Pro Cys Ile Thr Leu His Leu Val Leu
            180                 185                 190

His Tyr Phe Leu Ile Thr Asn Tyr Ala Trp Met Leu Cys Glu Gly Phe
        195                 200                 205

Tyr Leu His Thr Val Leu Val Ser Ala Phe Val Ser Glu Lys Lys Leu
    210                 215                 220

Val Lys Trp Leu Val Leu Gly Trp Thr Pro Ala Cys Val Ile
225                 230                 235                 240

Val Leu Tyr Gly Val Leu Arg Gly Thr Tyr Gly Thr Asp Glu Asp Val
                245                 250                 255

Thr Leu Cys Trp Met Thr Glu Ser Ser Tyr Gly Met Val Phe Ile Val
            260                 265                 270

Pro Val Cys Ile Ser Met Leu Leu Asn Leu Leu Phe Leu Cys Asn Ile
        275                 280                 285

Val Arg Val Val Leu Leu Lys Met Arg Ala Pro Ala Gly Pro Gln Gly
    290                 295                 300

Ser Gly Pro Ser Arg Thr Ile Leu Gln Ala Phe Arg Ala Thr Leu Leu
305                 310                 315                 320
```

Leu Val Pro Leu Leu Gly Leu Gln Tyr Met Leu Thr Pro Phe Arg Pro
            325                 330                 335

Asp Pro Gly His Pro Tyr Glu Arg Val Tyr Glu Thr Ile Ser Ala Phe
            340                 345                 350

Thr Ala Ser Phe Gln Gly Leu Phe Val Ala Val Leu Phe Cys Phe Phe
            355                 360                 365

Asn Gly Glu Val Ile Ala Gln Val Lys Arg Lys Trp Arg Thr Val Phe
370                 375                 380

Leu Arg Thr Arg Thr Asn Ser Tyr Thr Ala Thr Gln Val Ser Val Ser
385                 390                 395                 400

Lys Phe Leu Ile Lys Asp Ala Arg Arg Gln
            405                 410

<210> SEQ ID NO 53
<211> LENGTH: 544
<212> TYPE: PRT
<213> ORGANISM: Aedes aegypti

<400> SEQUENCE: 53

Met Phe Leu Arg Thr Ala Pro Ala Leu Gln Tyr Phe Ser Ser Ala Ser
1               5                   10                  15

Ser Asp Gly Tyr Arg Asn Asp Met Ala Ile Pro Gln Gly Gln Pro Ala
            20                  25                  30

Ile Pro Asn Gln Gln Asn Asn Phe Thr Ala Tyr Gln Asn Thr Lys Asn
            35                  40                  45

Trp Lys Asn Ile Ser Gln Cys Val Met Phe Pro Met Lys Ile Ser Phe
50                  55                  60

Ala Phe Phe Ala Leu Leu Met Leu Ser Ile Phe Thr Ala Val Thr Val
65                  70                  75                  80

Leu Arg Ser Ile Ser Ala Ser Asn Ala Arg His Asp Gln Gln Thr Gln
            85                  90                  95

Leu Phe Cys Pro Arg Arg Phe Asp Gly Trp Thr Cys Trp Glu Ser Gln
            100                 105                 110

Pro Ala Gly Thr Ile Ala Gln Asn Phe Cys Pro Asn Phe Val Leu Gly
            115                 120                 125

Phe Asp Ala Ser Arg Leu Ala Tyr Arg Ile Cys His Ala Asn Gly Ser
            130                 135                 140

Trp Phe Thr His Pro Glu Ser Gly Arg Glu Trp Ser Asn Tyr Thr Asn
145                 150                 155                 160

Cys Ile Asp Val Asp Asp Met Lys Phe Arg Arg Leu Val Asn Asp Leu
            165                 170                 175

Tyr Ile Gly Gly Tyr Thr Ile Ser Leu Val Thr Leu Ile Val Ser Leu
            180                 185                 190

Cys Val Phe Phe Ser Phe Arg Thr Leu Lys Cys Thr Arg Ile Arg Ile
            195                 200                 205

His Ile Asn Leu Phe Thr Ser Leu Ala Leu Ser Cys Ala Phe Trp Ile
            210                 215                 220

Leu Trp Tyr Lys Phe Val Val Glu Asp Pro Asp Val Thr Asn Arg Asn
225                 230                 235                 240

Gly Val Ser Ala Ser Val Thr Gln Val Cys Cys Lys Glu Ala Lys Ile
            245                 250                 255

Thr Pro Met Phe Asn Lys Val Phe Ser Ile Arg Phe Gln Asn Trp Cys
            260                 265                 270

Ile Ala Leu His Ile Leu Leu His Tyr Leu Met Leu Val Asn Tyr Phe

```
                275                 280                 285
Trp Met Phe Cys Glu Gly Leu Gln Leu His Leu Val Leu Val Ile Val
    290                 295                 300
Met Gln Ser Val Pro Pro Leu Gln Arg Cys Cys Ile Tyr Ser Asn Phe
305                 310                 315                 320
Gln Trp Lys Leu Asn Ile Thr Glu Arg Arg Pro Ser Phe Leu Gly Gly
                325                 330                 335
Asn Glu Asn Leu Ser Val Tyr Tyr Glu Gln Ala Gln Thr Tyr Ser Asp
                340                 345                 350
Ser Asn Arg His Gln Pro Pro Ser Ser Phe Ala Glu Gly Lys Ser
                355                 360                 365
Ile Phe Leu Met Ser Phe Phe Thr Leu Thr Pro Thr His Val His Val
                370                 375                 380
Ala Ile Phe Phe Leu Leu Ser Ile Arg Phe Ser Cys Trp Met Asn Glu
385                 390                 395                 400
Ser His Ala Met Trp Leu Leu Thr Ile Pro Val Cys Phe Ser Leu Val
                405                 410                 415
Ala Ser Leu Val Phe Leu Ile Asn Val Val Arg Val Leu Leu Thr Lys
                420                 425                 430
Leu Asn Ser Thr Ser Pro Asn Pro Ala Pro Leu Gly Leu Lys Lys Ala
                435                 440                 445
Thr Arg Ala Thr Leu Ile Leu Ile Pro Leu Phe Gly Leu Gln His Ile
                450                 455                 460
Leu Leu Pro Phe Arg Pro Asp Lys Gly Cys Glu Leu Glu Arg Tyr Tyr
465                 470                 475                 480
Gln Val Val Ser Ala Val Leu Ile Ser Leu Gln Gly Ala Cys Val Ser
                485                 490                 495
Cys Leu Phe Cys Phe Ala Asn His Asp Val Ile Phe Ala Ile Lys Cys
                500                 505                 510
Gln Leu Ser Arg Phe Phe Pro Thr Leu Val His His Pro Phe Arg Glu
                515                 520                 525
Ser Tyr Asn Gly Gly Gln Pro Ala Thr Gln Ser Arg Asp Met Val Val
                530                 535                 540

<210> SEQ ID NO 54
<211> LENGTH: 544
<212> TYPE: PRT
<213> ORGANISM: Ixodes scapularis

<400> SEQUENCE: 54

Met Phe Leu Arg Thr Ala Pro Ala Leu Gln Tyr Phe Ser Ser Ala Ser
1               5                   10                  15
Ser Asp Gly Tyr Arg Asn Asp Met Ala Ile Pro Gln Gly Gln Pro Ala
                20                  25                  30
Ile Pro Asn Gln Gln Asn Asn Phe Thr Ala Tyr Gln Asn Thr Lys Asn
                35                  40                  45
Trp Lys Asn Ile Ser Gln Cys Val Met Phe Pro Met Lys Ile Ser Phe
            50                  55                  60
Ala Phe Phe Ala Leu Leu Met Leu Ser Ile Phe Thr Ala Val Thr Val
65              70                  75                  80
Leu Arg Ser Ile Ser Ala Ser Asn Ala Arg His Asp Gln Gln Thr Gln
                85                  90                  95
Leu Phe Cys Pro Arg Arg Phe Asp Gly Trp Thr Cys Trp Glu Ser Gln
                100                 105                 110
```

-continued

Pro Ala Gly Thr Ile Ala Gln Asn Phe Cys Pro Asn Phe Val Leu Gly
115                 120                 125

Phe Asp Ala Ser Arg Leu Ala Tyr Arg Ile Cys His Ala Asn Gly Ser
130                 135                 140

Trp Phe Thr His Pro Glu Ser Gly Arg Glu Trp Ser Asn Tyr Thr Asn
145                 150                 155                 160

Cys Ile Asp Val Asp Asp Met Lys Phe Arg Arg Leu Val Asn Asp Leu
            165                 170                 175

Tyr Ile Gly Gly Tyr Thr Ile Ser Leu Val Thr Leu Ile Val Ser Leu
        180                 185                 190

Cys Val Phe Phe Ser Phe Arg Thr Leu Lys Cys Thr Arg Ile Arg Ile
    195                 200                 205

His Ile Asn Leu Phe Thr Ser Leu Ala Leu Ser Cys Ala Phe Trp Ile
210                 215                 220

Leu Trp Tyr Lys Phe Val Val Glu Asp Pro Asp Val Thr Asn Arg Asn
225                 230                 235                 240

Gly Val Ser Ala Ser Val Thr Gln Val Cys Cys Lys Glu Ala Lys Ile
            245                 250                 255

Thr Pro Met Phe Asn Lys Val Phe Ser Ile Arg Phe Gln Asn Trp Cys
        260                 265                 270

Ile Ala Leu His Ile Leu Leu His Tyr Leu Met Leu Val Asn Tyr Phe
    275                 280                 285

Trp Met Phe Cys Glu Gly Leu Gln Leu His Leu Val Leu Val Ile Val
290                 295                 300

Met Gln Ser Val Pro Pro Leu Gln Arg Cys Cys Ile Tyr Ser Asn Phe
305                 310                 315                 320

Gln Trp Lys Leu Asn Ile Thr Glu Arg Arg Pro Ser Phe Leu Gly Gly
            325                 330                 335

Asn Glu Asn Leu Ser Val Tyr Tyr Glu Gln Ala Gln Thr Tyr Ser Asp
        340                 345                 350

Ser Asn Arg His Gln Pro Pro Ser Ser Ser Phe Ala Glu Gly Lys Ser
    355                 360                 365

Ile Phe Leu Met Ser Phe Phe Thr Leu Thr Pro Thr His Val His Val
370                 375                 380

Ala Ile Phe Phe Leu Leu Ser Ile Arg Phe Ser Cys Trp Met Asn Glu
385                 390                 395                 400

Ser His Ala Met Trp Leu Leu Thr Ile Pro Val Cys Phe Ser Leu Val
            405                 410                 415

Ala Ser Leu Val Phe Leu Ile Asn Val Val Arg Val Leu Leu Thr Lys
        420                 425                 430

Leu Asn Ser Thr Ser Pro Asn Pro Ala Pro Leu Gly Leu Lys Lys Ala
    435                 440                 445

Thr Arg Ala Thr Leu Ile Leu Ile Pro Leu Phe Gly Leu Gln His Ile
450                 455                 460

Leu Leu Pro Phe Arg Pro Asp Lys Gly Cys Glu Leu Glu Arg Tyr Tyr
465                 470                 475                 480

Gln Val Val Ser Ala Val Leu Ile Ser Leu Gln Gly Ala Cys Val Ser
            485                 490                 495

Cys Leu Phe Cys Phe Ala Asn His Asp Val Ile Phe Ala Ile Lys Cys
        500                 505                 510

Gln Leu Ser Arg Phe Phe Pro Thr Leu Val His His Pro Phe Arg Glu
    515                 520                 525

```
Ser Tyr Asn Gly Gly Gln Pro Ala Thr Gln Ser Arg Asp Met Val Val
530                 535                 540
```